US012805777B2

(12) United States Patent
Burnes et al.

(10) Patent No.: US 12,805,777 B2
(45) Date of Patent: *Nov. 24, 2026

(54) MARKER MONITORING VIA A MEDICAL DEVICE

(71) Applicant: Medtronic, Inc., Minneapolis, MN (US)

(72) Inventors: John E. Burnes, Blaine, MN (US); James K. Carney, Roseville, MN (US); Jonathan L. Kuhn, Ham Lake, MN (US); Mark J. Phelps, Scottsdale, AZ (US); Jesper Svenning Kristensen, Virum (DK); Rodolphe Katra, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 107 days.

This patent is subject to a terminal disclaimer.

(21) Appl. No.: 18/972,232

(22) Filed: Dec. 6, 2024

(65) Prior Publication Data

US 2025/0098993 A1 Mar. 27, 2025

Related U.S. Application Data

(63) Continuation of application No. 18/469,257, filed on Sep. 18, 2023, now Pat. No. 12,171,554, which is a (Continued)

(51) Int. Cl.

*A61B 5/1459* (2006.01)
*A61B 5/00* (2006.01)

(Continued)

(52) U.S. Cl.

CPC .......... *A61B 5/1459* (2013.01); *A61B 5/0031* (2013.01); *A61B 5/0036* (2018.08);

(Continued)

(58) Field of Classification Search

CPC . A61B 5/1459; A61B 5/14546; A61B 5/4833; A61B 5/4848; A61B 5/4866; A61B 5/4381; A61B 5/6861; A61B 5/7278

See application file for complete search history.

(56) References Cited

U.S. PATENT DOCUMENTS 5,117,824 A 6/1992 Keimel et al.
6,049,727 A 4/2000 Crothall (Continued)

FOREIGN PATENT DOCUMENTS

WO 2004075032 A2 9/2004
WO 2005043157 A2 5/2005
WO 2007137037 A1 11/2007

OTHER PUBLICATIONS

"Interview with PhiloMetron CEO Darrel Drinan," retrieved from https://www.wearable-technologies.com/2012/06/interview-with-philometron-ceo-darrel-drinan/, Jun. 5, 2012, 2 pp.

(Continued)

*Primary Examiner* — Eric F Winakur

(74) *Attorney, Agent, or Firm* — Shumaker & Sieffert, P.A.

(57) ABSTRACT

In some examples, a medical system includes a medical device. The medical device may include a housing configured to be implanted in a target site of a patient, a light emitter configured to emit a signal configured to cause a fluorescent marker to emit a fluoresced signal into the target site, and a light detector that may be configured to detect the fluoresced signal. The medical system may include processing circuitry configured to determine a characteristic of the fluorescent marker based on the emitted signal and the fluoresced signal. The characteristic of the fluorescent marker may be indicative of a presence of a compound in the patient, and the processing circuitry may be configured to (Continued)

track the presence of the compound of the patient based on the characteristic of the fluorescent marker.

20 Claims, 14 Drawing Sheets

Related U.S. Application Data continuation of application No. 17/306,474, filed on May 3, 2021, now Pat. No. 11,759,131, which is a continuation of application No. 16/122,289, filed on Sep. 5, 2018, now Pat. No. 11,013,436.

(60) Provisional application No. 62/554,849, filed on Sep. 6, 2017.

(51) Int. Cl.

| | |
|---|---|
| ***A61B 5/0205*** | (2006.01) |
| ***A61B 5/024*** | (2006.01) |
| ***A61B 5/07*** | (2006.01) |
| ***A61B 5/08*** | (2006.01) |
| ***A61B 5/145*** | (2006.01) |
| ***A61B 5/1473*** | (2006.01) |
| ***A61B 5/20*** | (2006.01) |
| ***A61M 5/142*** | (2006.01) |
| ***A61M 5/172*** | (2006.01) |
| ***A61N 1/375*** | (2006.01) |
| ***G01N 21/01*** | (2006.01) |
| ***G01N 21/64*** | (2006.01) |

(52) U.S. Cl.

CPC ........ *A61B 5/0071* (2013.01); *A61B 5/02055* (2013.01); *A61B 5/076* (2013.01); *A61B 5/14507* (2013.01); *A61B 5/14546* (2013.01); *A61B 5/14735* (2013.01); *A61B 5/201* (2013.01); *A61B 5/4381* (2013.01); *A61B 5/4833* (2013.01); *A61B 5/4839* (2013.01); *A61B 5/4848* (2013.01); *A61B 5/4866* (2013.01); *A61B 5/686* (2013.01); *A61B 5/6861* (2013.01); *A61B 5/7278* (2013.01); *A61N 1/3756* (2013.01); *G01N 21/6408* (2013.01); *G01N 21/6428* (2013.01); *A61B 5/02405* (2013.01); *A61B 5/08* (2013.01); *A61M 5/14276* (2013.01); *A61M 5/1723* (2013.01); *A61M 2205/3523* (2013.01); *A61M 2205/3553* (2013.01); *G01N 2021/0143* (2013.01); *G01N 2021/6417* (2013.01); *G01N 2021/6441* (2013.01)

(56) References Cited

U.S. PATENT DOCUMENTS

| | | | |
|---|---|---|---|
| 6,280,703 | B1 | 8/2001 | Combs et al. |
| 6,663,846 | B1 | 12/2003 | McCombs et al. |
| 7,378,056 | B2 | 5/2008 | Black |
| 7,510,699 | B2 | 3/2009 | Black et al. |
| 8,129,191 | B2 | 3/2012 | Sheard et al. |
| 8,249,697 | B2 | 8/2012 | Holschneider et al. |
| 8,271,080 | B2 | 9/2012 | Thompson et al. |
| 9,075,910 | B2 | 7/2015 | Bhavaraju et al. |
| 10,548,536 | B2 | 2/2020 | Nam et al. |
| 11,013,436 | B2 | 5/2021 | Burnes et al. |
| 11,759,131 | B2 | 9/2023 | Burnes et al. |
| 12,171,554 | B2 | 12/2024 | Burnes et al. |
| 2002/0102212 | A1 | 8/2002 | Black |
| 2002/0111542 | A1 | 8/2002 | Warkentin et al. |
| 2004/0081587 | A1 | 4/2004 | Melker et al. |
| 2004/0197267 | A1 | 10/2004 | Black et al. |
| 2005/0137481 | A1 | 6/2005 | Sheard et al. |
| 2006/0206067 | A1 | 9/2006 | Ferek-Petric |
| 2008/0213904 | A1 | 9/2008 | Sliwa et al. |
| 2008/0288027 | A1 | 11/2008 | Kroll et al. |
| 2008/0294209 | A1 | 11/2008 | Thompson et al. |
| 2010/0099992 | A1 | 4/2010 | Holschneider et al. |
| 2010/0312128 | A1 | 12/2010 | Karst et al. |
| 2011/0224912 | A1 | 9/2011 | Bhavaraju et al. |
| 2012/0330116 | A1 | 12/2012 | Eggers et al. |
| 2014/0276928 | A1 | 9/2014 | Vanderpool et al. |
| 2015/0165213 | A1 | 6/2015 | Ebert et al. |
| 2016/0310031 | A1 | 10/2016 | Sarkar |
| 2017/0173262 | A1 | 6/2017 | Veltz |

OTHER PUBLICATIONS

"Product Development Scientific Support Department Qualification Opinion," European Medicines Agency, accessed on Jun. 24, 2016, from http://www.ema.europa.eu/docs/en_GB/document_library/Regulatory_and_procedural_guideline/2015/09/WC500193612.pdf, Aug. 7, 2015, 25 pp.

"Remote Monitoring," Novartis, accessed on Jun. 24, 2016, from https://www.novartis.com/our-work/innovation/remote-monitoring, 2 pp.

Sicel Technologies, Inc. Receives U.S. Food & Drug Administration Clearance for DVS®-HFT, a Next-Generation Wireless Sensor to Measure Actual Radiation Dose at Breast and Prostate Tumor Site, retrieved from http://www.businesswire.com/news/home/20090309005108/en/Sicel-Technologies-Receives-U.S.-Food-Drug-Administration, Mar. 9, 2009, 2 pp.

"The Renal Function System," MediBeacon, accessed on Sep. 5, 2018 from http://www.medibeacon.com/products/nephrology/renal-function-system/, 3 pp.

Communication pursuant to Article 94(3) EPC from counterpart European Application No. 18786894.8 dated Feb. 6, 2023, 7 pp.

First Office Action and Search Report, and translation thereof, from Chinese Application No. 201880057733.5 dated Jul. 12, 2022, 15 pp.

Prosecution History from U.S. Appl. No. 16/122,289, dated Oct. 28, 2020 through Jan. 27, 2021, 27 pp.

Prosecution History from U.S. Appl. No. 17/306,474, now issued U.S. Pat. No. 11,759,131, dated Mar. 2, 2023 through Jun. 20, 2023, 23 pp.

Prosecution History from U.S. Appl. No. 18/469,257, now issued U.S. Pat. No. 12,171,554, dated Aug. 16, 2024 through Nov. 4, 2024, 25 pp.

Office Action from counterpart Chinese Application No. 201880057733.5 dated Jul. 29, 2026, 6 pp. Only translation available.

MARKER MONITORING VIA A MEDICAL DEVICE

This application is a continuation of U.S. patent application Ser. No. 18/469,257, filed on Sep. 18, 2023, which is a continuation of U.S. patent application Ser. No. 17/306,474, filed on May 3, 2021, now issued as U.S. Pat. No. 11,759, 131, which is a continuation of U.S. patent application Ser. No. 16/122,289, filed on Sep. 5, 2018, now issued as U.S. Pat. No. 11,013,436, which claims the benefit of U.S. Provisional Patent Application No. 62/554,849, filed on Sep. 6, 2017. The entire content of each of these applications is incorporated herein by reference.

TECHNICAL FIELD

This disclosure relates to medical devices, and more particularly, to techniques for monitoring a state of a patient with a medical device.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads to position electrodes or sensors at a desired location, or may be leadless, with the ability to wirelessly transmit data either to another device implanted in the patient or to another device located externally of the patient, or both.

Some implantable medical devices may be used to chronically monitor physiological signals of the patient, such as implantable hemodynamic monitors, implantable cardiac monitors (sometimes referred to as implantable loop recorders or electrocardiogram monitors), implantable blood chemistry monitors, implantable pressure monitors, or the like. Other implantable devices may be configured to deliver a therapy in conjunction with or separate from the monitoring of physiological signals.

SUMMARY

This disclosure, among other things, describes systems and techniques for tracking a fluorescent marker administered to a patient. In an example, the fluorescent marker (also may be referred to as a "fluorescent tracer" or a "marker compound") may be ingested by the patient or may be injected into the patient. The fluorescent marker may be tracked using light sensors (also may be referred to as "optical sensors"), such as may be disposed on an implantable medical device (IMD) or an external medical device. One or more characteristics of the fluorescent marker may be tracked over time. Additionally, one or more fluorescent markers may be used, such that one or more characteristics of each of the fluorescent markers may be tracked over time. By tracking the fluorescent marker, such as described herein, data may be generated and used to improve patient care and patient outcomes. Moreover, therapy may be initiated or adjusted to better treat the patient.

In an example, this disclosure is directed to a medical system comprising a medical device comprising: a housing configured to be implanted in a target site of a patient; a light emitter on or within the housing, the light emitter configured to emit a signal into the target site, wherein the emitted signal is configured to cause a fluorescent marker within the patient to emit a fluoresced signal; and a light detector on or within the housing, the light detector configured to detect the fluoresced signal; and processing circuitry at least partially within the housing and coupled to the light emitter and the light detector, the processing circuitry configured to determine a characteristic of the fluorescent marker based on the emitted signal and the fluoresced signal, wherein the characteristic of the fluorescent marker is indicative of at least one of a presence of a compound in the patient or a physiological function of the patient, and wherein the processing circuitry is configured to track the presence of the compound of the patient based on the characteristic of the fluorescent marker.

In an example, this disclosure is directed to a method for tracking a fluorescent marker within a patient, the method comprising: controlling a light emitter coupled to processing circuitry to emit a signal into a target site of the patient, wherein the signal is configured to cause the fluorescent marker within the patient to emit a fluoresced signal; detecting, by a light detector coupled to the processing circuitry, the fluoresced signal; determining, by the processing circuitry, a characteristic of the fluorescent marker based on the emitted signal and the fluoresced signal, wherein the characteristic of the fluorescent marker is indicative of at least one of a presence of a compound in the patient or a physiological function of the patient; and tracking, by the processing circuitry, the presence of the compound in the patient based on the characteristic of the fluorescent marker.

In an example, this disclosure is directed to non-transitory, computer-readable storage medium comprising instructions, that when executed, cause one or more processors to: control a light emitter coupled to the one or more processors to emit a signal into a target site of the patient, wherein the signal is configured to cause a fluorescent marker within the patient to emit a fluoresced signal; detect, by a light detector coupled to the one or more processors, the fluoresced signal; and determine a characteristic of the fluorescent marker based on the emitted signal and the fluoresced signal, wherein the characteristic of the fluorescent marker is indicative of at least one of a presence of a compound within the patient or a physiological function of the patient; and track the presence of the compound in the patient based on the characteristic of the fluorescent marker.

In an example, this disclosure is directed to a system comprising: means for controlling a light emitter to emit a signal into a target site of a patient, wherein the signal is configured to cause a fluorescent marker within the patient to emit a fluoresced signal; means for detecting, by a light detector, the fluoresced signal; and means for determining a characteristic of the fluorescent marker based on the emitted signal and the fluoresced signal, wherein the characteristic of the fluorescent marker is indicative of at least one of a presence of a compound within the patient or a physiological function of the patient; and means for tracking the presence of the compound in the patient based on the characteristic of the fluorescent marker.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

Figure 1:
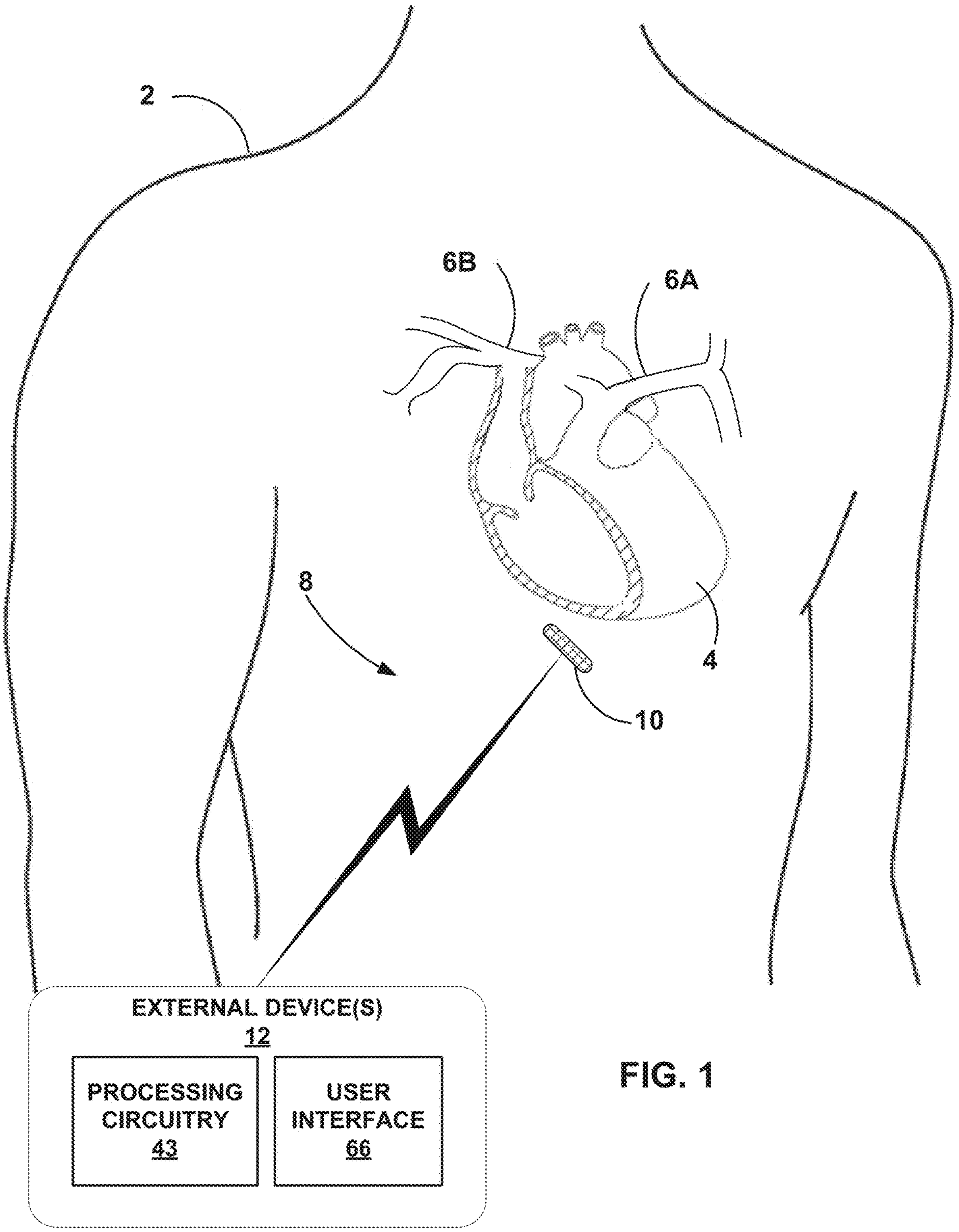
FIG. 1 is a conceptual drawing illustrating an example of a medical system in conjunction with a patient.

The details of one or more examples of this disclosure are set forth in the accompanying drawings and the description below. Other features, objects, and advantages of this disclosure will be apparent from the description and drawings, and from the claims.

DETAILED DESCRIPTION

In this disclosure, techniques, systems, devices, components, assemblies, and methods for tracking a characteristic of a fluorescent marker in a patient are described. In an example, an IMD (also may be referred to as an "insertable medical device" or an "insertable cardiac monitor") may be configured to be implanted in a target site of the patient. The IMD may be a relatively small device, and may be placed (e.g., inserted) under the skin of the patient's chest. The IMD may be a part of a medical device system (also may be referred to as a "medical system" or a "system") that includes other devices. For example, the system may include one or more other implanted devices, one or more external devices, or both, such as described with respect to FIG. 5 herein. In some examples, the IMD includes a light emitter, a light detector, and processing circuitry. The light emitter may be configured to emit a signal (e.g., a light signal) into the target site of the patient. The target site may include a site proximate to a blood vessel or a subcutaneous site proximate to the heart of the patient. In some examples, the target site includes any well-vascularized tissue. Well-vascularized tissue may include, among other things, tissue with sufficient blood flow to carry out the techniques described herein.

When the fluorescent marker administered into the patient is present (e.g., within the functional signal range of the light emitter), the emitted signal may cause the fluorescent marker to emit a fluoresced signal. The light detector may be configured to detect the fluoresced signal. As such, for example, the processing circuitry is configured to determine a characteristic of the fluorescent marker based on the emitted signal and the fluoresced signal. The characteristic of the fluorescent marker may be indicative of a physiological phenomenon of the patient. In an example, the characteristic of the fluorescent marker may be indicative of a presence of a compound (e.g., the fluorescent marker, a drug, or another compound). The processing circuitry may be configured to track the characteristic of the fluorescent marker. By using the systems and techniques described herein, IMDs may be improved, for example, by gaining more functionality in a minimally invasive design that improves patient medication compliance tracking, organ (e.g., kidney, liver, or another organ) function monitoring, and biomarker monitoring, among other things. In general, the term "medication" and the term "drug" may be used interchangeably herein. The systems and techniques described herein may improve medication safety, such as by tracking the characteristic of the fluorescent marker and providing information to a user about the tracked characteristic.

The processing circuitry may be configured to determine the characteristic of the fluorescent marker based on information, in addition to or as an alternative to, the emitted signal and the fluoresced signal. For example, such information may include fluorescent marker information (e.g., shape of emission spectrum on a graph of emission wavelength (in nanometers) to relative intensity units, the excitation spectrum or other fluorescent response data, what type of light is used to cause the luminescence, fluorescence lifetime or other information). The fluorescence lifetime characteristic may be a measure of an amount of time that a fluorophore or marker is in an excited state before returning to its ground state, and the lifetime characteristic may be useful because a reference measurement may not be required. In an example, the fluorescence lifetime characteristic may be directly measured (e.g., processing circuitry initiates a timer when the light emitter emits light into, for example, well-vascularized tissue, and stops the timer when the fluoresced signal is detected by the light detector). In an example, fluorescence may refer to absorbing and reemission of light. The light used to excite the fluorescent marker (e.g., a fluorophore) may be referred to as an excitation source (e.g., a light emitter). The light detector may be configured to detect light at different wavelengths. In some examples, the light detector includes a monochrometer, such as may allow the detector only to detect a narrow spectrum of wavelengths of light. In other examples, the light detector includes an optical filter that allows only a narrow spectrum of light to be detected. Other light detectors may be used. In some examples, multiple light emitters or multiple light detectors are used. By using an IMD that includes both light sensors and other sensors (e.g., cardiac monitoring sensors), a more nuanced view of the patient's health and state may be obtained, and therefore, better treatments may be provided to the patient.

In an example, the systems and techniques described herein may include using a marker or material comprising unique absorption spectra, such as may be used with direct spectroscopy (e.g., instead of fluorescence). In an example, such a marker or material may comprise a high absorption at or around 800 nanometers (nm) and a low absorption at or around 1100 nm (e.g., which may be different than that of hemoglobin, and as contrasted to that of water). As such, in some examples, the IMD may include appropriate components (e.g., which may include the light detector) to measure the two wavelengths. In an example, the IMD comprises a spectrometer or a spectrum analyzer configured to measure the two wavelengths. Processing circuitry of the IMD may compute a ratio of the two wavelengths, for example, and may determine the presence of the marker or material based on an elevated absorption at 800 nm relative to 1100 nm. Although described with respect to 800 nm and 1100 nm in this example, a marker or material may comprise different high and low absorption characteristics (e.g., including a high absorption from about 300 nm to about 1200 nm, and a low absorption from about 900 nm to about 4000 nm).

One aspect of this disclosure includes systems and methods for tracking the characteristic of a marker. The marker may be, but is not necessarily, fluorescent. Examples described herein in the context of fluorescent marker are equally applicable to non-fluorescent markers (e.g., reflective markers), such as those including unique absorption spectra as described above. The characteristic of the fluorescent marker may be indicative of a physiological phenomenon of the patient. The characteristic, in some examples, is an amount or concentration of the fluorescent marker in the patient, a metabolism profile of the fluorescent marker (e.g., an amount of a drug or marker processed by the patient over time, such as may be displayed in the form of a graph or a table of values), an intensity of a fluoresced signal, a frequency of the fluoresced signal (e.g., emission frequency), the fluorescence lifetime or other signal information, or another characteristic related to the fluorescent marker. The physiological phenomenon of the patient may include, in some examples, a drug metabolism profile for the patient, a high-risk event, heart failure, a change in fluid or pressure (e.g., a fluid increase, such as pulmonary edema), an organ clearance profile, a presence of a biomarker, or another physiological phenomenon.

As such, for example, a fluorescent marker corresponding to a drug (e.g., similar metabolism profiles, the fluorescent marker being bonded to the drug, or another relation), may be tracked, which may provide information about the drug metabolism. For example, a change in the amount of fluorescent marker over time may provide insight into a patient's medication compliance. In an example, the change in the amount of the fluorescent marker measured over time may be based on an amplitude of a fluoresced signal. In an example, the change in the amount of the fluorescent marker may be based on an intensity of the fluoresced signal, such as measured using the light detector. In general, the amount of the fluorescent marker may be measured in the space around the target site that the emitted signal may reach and where light detector may receive the fluoresced signal from.

In some examples, the systems and techniques described herein may be include or be used with an external device instead of an implantable device. For example, a device including a light emitter and a light detector as described herein may be an external patch or other external device positionable on the patient. In such examples, processing circuitry configured to determine a characteristic of a fluorescent marker (e.g., an amount or concentration) may be included within the patch or included within another external device. In some such examples, a device in the form of an external patch may be affixed to the patient's skin, such as by an adhesive. For example, the patch may be positionable on the patient such that the light emitter and light detector face the skin of the patient, such that the space where the amount or concentration of the fluorescent marker is measured may include the tissue directly below the patch. In examples in which the medical device comprises and an IMD (e.g., an ICM), the space where the amount of the fluorescent marker is measured may include the tissue (e.g., well-vascularized tissue) immediately surrounding the IMD.

The systems and techniques herein may include monitoring a patient's medication use, underlying physiology, or one or more pathophysiologies. The fluorescent marker described herein may be a biocompatible material. In general, by using the light emitter on a relatively small IMD, as described herein, to emit a light signal (e.g., a green light signal) at a fluorescent marker, the fluoresced signal (e.g., a red-light signal) may be detected by a light detector on the IMD. In general, for example, the emitted light signal and the fluoresced signal may have different wavelengths, such as different wavelength bands. Either or both of the emitted and fluoresced signals may be visible or not visible, e.g., infrared or near infrared (NIR). Characteristics about the signals, such as amplitude, time decay, or intensity may be used to determine information about the fluorescent marker, and thus indirectly, to determine information about a physiological phenomenon of which a characteristic of the fluorescent marker may be indicative.

In an example, by using the systems and techniques described herein, the efficacy of a medication may be determined. For example, the IMD described herein may determine whether one or two pills of a particular drug have been taken by the patient. In an example, the IMD may determine how quickly the drug is washed out of the patient's body. In an example, the IMD may determine an appropriate treatment regimen for the patient, such as a change in dosage. In some examples, another device (e.g., local or remote) may make these or other determinations. As described below, the medical system may include multiple internal or external devices in addition to the IMD, and one or more of these devices may perform the techniques described herein, such as determining the efficacy of the medication.

In another example, by using the systems and techniques described herein, a patient compliance with a medication regimen may be determined. For example, processing circuitry of an IMD or external device (e.g., a patient mobile device or other external device) described herein may determine the patient's compliance with the medication regimen based on information about the medication regimen stored in a memory of the IMD or external device. In some such examples, an external device may be configured to provide a reminder to the patient and/or a caregiver for the patient to take the medication if the processing circuitry determines that the patient is not compliant with the medication regimen and/or if the processing circuitry determines that a time period between doses of the medication according to the medication regimen has elapsed. Additionally, or alternatively, the external device may provide a notification to clinician indicating whether the patient is compliant with the medication regimen and/or when the patient has taken the medication.

The IMD may emit signals and measure information from inside the patient (e.g., from blood, interstitial fluid, urine, an organ, or another patient structure or fluid). For example, the light emitter may emit a cloud of light (e.g., non-directional) in the implantation site of the IMD. The light may cause a fluorescent marker present, for example in the blood, to fluoresce, thus emitting the fluoresced signal detected by the light detector.

In an example, the medical system described herein may use or merge the information about the tracked fluorescent marker with other information. Such other information may be therapeutic information or diagnostic information. Such information may come from sources such as cardiac information from the insertable cardiac monitor, information from a pulmonary artery pressure monitor, information from an implantable cardiac defibrillator, information from a cardiac resynchronization therapy device, information from medication compliance records, information about patient physiological parameters such as blood pressure, information from electronic health records, information from electronic medical records, or other sources. Communication between systems and devices to merge such information may be accomplished, for example, using communication techniques described with respect to FIG. 5. The medical system may analyze the information. In some examples, the systems and techniques described herein include providing an indication, based on data analytics, such as patient compliance, or more complex indications, such as may help to ensure compliance and safer, more informed medication titration. As such, by tracking a fluorescent marker as described herein, medical systems may be improved by providing safer instructions to patients about medications, for example.

In an example, the systems and techniques described herein may include systems and techniques for tailoring dosage (e.g., drug dosage or marker amount), to a particular patient. In general, dosages may be set based on population data, and each patient may respond differently to a given dosage. By tailoring dosage using the techniques and systems described herein, better patient outcomes may be achieved, including better compliance and safer drug dosing based on the particular patient's response to a particular dosage and/or pattern of medication taking compliance.

For example, by tracking a fluorescent marker as described herein during an initial "training" period, information such as about the patient's compliance and response to the drug dosage may be determined. As such, the physician may prescribe a dosage for the training period (e.g., 2 weeks, 1 month, 40 days, or another period). The systems and devices may monitor patient compliance and the patient drug response, as described further herein, for the training period, such as may be with respect to kidney function. In an example, at the conclusion of the training period, information about the tracked marker over time may be used by the physician to tailor the dosage to that patient's response and/or compliance.

In an example, at the conclusion of the initial training period, the training may further comprise a second training period. The physician may prescribe a different dosage for the second training period, such as based on the information about the tracked marker. The systems and devices may monitor for both compliance and patient response during the second training period. At the conclusion of the second training period, the information about patient response and compliance may be used by the physician to tailor the dosage for that patient. By tailoring the dosage using the systems and techniques described herein, the systems and techniques may improve upon conventional dosage techniques.

In an example, tailoring dosage using the systems and techniques described herein may also occur based on factors such as natural variability of patient compliance or based on results of a change in medication, such as described further below with respect to an excursion such as heart failure. In an example, a patient may tend to be more compliant during weekdays and less compliant on weekends. By monitoring both compliance and patient health status, as described herein, information including trends of compliance (e.g., based on effective dosage) may be used to tailor that patient's dosage.

In an example, for longer acting or cumulative effect type medications, the systems and techniques may include identifying these kinds of compliance patterns. In an example, the pattern may be compensated for with dosage. For example, in the case of good compliance during the week, but poor compliance on the weekend for some medications the dosage may increase during the week by a factor of 7/5=1.4. In this way, the device may automatically help keep the patient in compliance by tracking the patient's behavior based on tracking the characteristic of the marker over time.

The systems and techniques described herein include systems and techniques for monitoring medication compliance of the patient. Many chronic conditions, such as heart failure or hypertension, may require that a patient takes one or more medications on a regular basis. The patient's failure to comply with a medication regimen may lead to poor outcomes. The present inventors have recognized, among other things, that if a clinician is not able to determine if the patient is taking medications or which medications the patient has been taking, then adjusting medications, either acutely or chronically, may be dangerous for the patient. As such, for example, a medical system may provide better understanding of the patient's medication compliance, such as may lead to better heart failure management. The terms "medications" and "drugs" as used herein may be used interchangeably, and may refer to one or more medications that the patient is taking or has been prescribed by a physician. The medical device system described herein may determine if the patient is taking their medications. For example, by determining a characteristic of a fluorescent marker, such as may correspond to a patient medication metabolism profile, and tracking the characteristic of the fluorescent marker, the medical system may determine if the patient is compliant with the medication regimen. In this way, the clinician may work with the patient to begin compliance, rather than, for example, doubling a dose or changing the medication. In some examples, the medical system determines the extent of patient compliance, such as if the patient is taking their medications, but not fully complying with the directions or prescription (e.g., amount, timing, taken with food or drink, et cetera). As such, the systems and techniques described herein may provide the clinician a better understanding of why patient compliance or lack thereof. This may allow the clinician to treat the root cause of the lack of compliance. Additionally or alternatively, there may be situations where a clinician, a payer, or a caregiver will want to know that a drug has been taken. For example, such a situation may include where a patient may be prone to forgetting to take their medication, where the medication may be very expensive, or where failure to take the medication might have relatively extreme consequences (e.g., a medication for a mental health issue). The medical system may provide alerts that include an indication of whether a drug has been taken.

As such, for example, the medical system may include output circuitry, such as may be coupled to the processing circuitry described herein. The output circuitry may be configured to provide an indication (such as a patient compliance indication). The output circuitry may provide the indication to another device within the medical system, such as a drug pump which may be instructed to begin or change a therapy. Additionally, or alternatively, the output circuitry may provide the indication to an external device that includes a user interface. For example, the indication may provide patient compliance information to a clinician. The patient compliance indication may be indicative of the patient's compliance in taking a medication (e.g., a prescribed medication, such as for heart failure or pulmonary edema). As described herein, the characteristic of the fluorescent marker may be indicative of the physiological phenomenon (e.g., the heart failure or the pulmonary edema), and as such, the processing circuitry may be configured to track the characteristic of the fluorescent marker, and determine the patient's compliance based on the characteristic of the fluorescent marker (e.g., including tracked over time).

The IMD may include optical sensors (e.g., light sensors) for acute or chronic monitoring of a tracer (e.g., the fluorescent marker) in the patient's blood or tissues. The terms "marker" and "tracer" may be used interchangeably herein. In some examples, the fluorescent marker may include a particular chemical with a characteristic reflective spectrum, such as may be used for a particular physiological phenomenon of interest. A clinician may determine which marker to be administered to the patient, in some examples. In other examples, the medical system may determine which marker should be used based on stored information, such as drug metabolism profiles and tracer metabolism profiles. Further description of the fluorescent marker is included herein.

Examples of the tracer may include compound of interest, such as sulfhemoglobin or methemoglobin, which may be associated with a medication level within a patent. In some such examples, the compound may be bound to a fluorescent marker. Additionally, or alternatively, the compound may itself be naturally fluorescent when exposed to light of a specific wavelength.

In some examples, one or more sensors of a medical device may be configured to detect a level (e.g., concentration) of a medication present within patient blood or tissue to determine the patient's compliance with a medication regimen. For a drug that is administered to the patient via ingestion (e.g., a pill or a capsule), the pill coating or capsule may comprise a tracer such as a fluorescent marker. The fluorescent marker may be administered along with the drug or may be co-packaged with the drug. For example, the fluorescent marker may be coated onto an exterior surface of the pill or capsule, or may be incorporated into other portions of the pill or capsule. As such, the fluorescent marker may be biocompatible with appropriate solubility. In some such examples, the fluorescent marker incorporated into a pill coating or capsule may be a fluorescing dye approved for food staining, such as a betalain-class dye that has been made fluorescent via bonding of the dye to a suitable fluorophore. Use of a fluorescent betalain dye may be desirable in some instances, as such dyes may be better able to pass through the patient's gastrointestinal tract (GI) and into the bloodstream than other dyes that are more hydrophilic than betalain and similar dyes (e.g., Indocyanine green, AF594, and other relatively more hydrophilic markers or dyes). In some instances, fluorescent markers that are better able to pass into the bloodstream may be advantageous for use in examples in which a pill or capsule for oral administration comprises a fluorescent marker. For example, fluorescent markers that are better able to pass into the bloodstream (e.g., in greater concentration than more hydrophilic markers) may diffuse into interstitial fluid (ISF) of the patient in a greater concentration than such other markers, which may better enable detection of the fluorescent marker by one or more sensors of a medical device.

In some examples, a fluorescent marker may be excitable using light at or above about 550 nm, may have distinct or easily recognizable emission spectra, may have a relatively high quantum yield and relatively short (e.g., nanosecond) fluorescence lifetime, and/or may have a pH and pO2 that are relatively insensitive to fluorescence. As such, the systems and techniques described herein include detecting an increase in the amount of the tracer in the blood or tissue, such as may include determining a threshold crossing or change in slope of the amount of the tracer. In some examples, the tracer may be time-released to provide an even release into the patient over a relatively longer period of time (e.g., the tracer itself may be formulated to be time-releasing in the patient). Additionally, or alternatively, the tracer may be bound to a molecule that is present in abundance within the patient (e.g., glucose). In some examples, binding the tracer to such a molecule may help prevent the tracer from being cleared faster than it is absorbed, and thus may reduce a possibility of the tracer being cleared before the medical system including the IMD can detect a signal.

In some examples, the medical system (e.g., the IMD), may include input circuitry that may be coupled to the processing circuitry. The input circuitry may be configured to receive information about the medication with respect to the patient, information about the fluorescent marker (e.g., as described herein), or other information. The processing circuitry may be configured to determine a medication level (e.g., an amount of medication in the patient, an amount of medication metabolized, or an amount yet to be metabolized), such as based on the information about the medication and the characteristic of the fluorescent marker. In some examples, the information about the medication includes, an administration time, a dosage, a medication type, an anticipated medication metabolism profile, medication history, other medication parameters or information, or any combination thereof. In some examples, such information may help enable the medical system to determine whether a dosage of the medication is adequate or otherwise appropriate for the patient.

The system may log the time a medication was taken, the dose of the medication, and biological levels reached of the medication at various times. Using the systems and techniques described herein, IMDs may determine and log the rate (e.g., how quickly) a drug is metabolized. Although not required to accomplish this and other functions, the IMD described herein may communicate with other devices to determine an actual medication metabolism rate of the drug by the patient. As such, an insertable cardiac monitor, for example, may include fluorescent marker tracking components in a minimally invasive design, that may improve patient outcomes while improving patient comfort, drug therapy effectiveness, and enable more efficient patient-clinician interactions.

As described herein, the fluorescent marker may have a similar metabolization profile to the target medication. In such examples, the marker and the medication may be absorbed and metabolized or cleared in a similar period of time. Additionally, or alternatively, the fluorescent marker may be attached to molecules of the medication in a particular ratio (e.g., 1:1 or any other suitable ratio), such that the ratio of the respective concentrations of the marker and the medication are known, at least initially upon administration of the medication. In some examples, the metabolization profile of the fluorescent marker may be calibrated to the medication, and such calibration parameters may be stored in the memory of the IMD. The IMD may determine and use techniques (e.g., algorithms) that use the data about the metabolization profiles of the marker and the drug for creating a drug regimen (e.g., a drug administration plan, including dose and timing).

As described herein, the physiological phenomenon may comprise an actual medication metabolism of the patient (e.g., a profile, a measure, or a value), and the processing circuitry may be configured to determine a measure (e.g., how quickly the drug is metabolized, or a measure over time, acutely or chronically, depending on the disease state) of the actual medication metabolism based on the information about the medication and the characteristic of the fluorescent marker. The systems and techniques described herein may include tracking the presence of a compound in the patient, such as a medication or drug. For example, the characteristic of the fluorescent marker may be indicative of an amount of the compound in the blood. Any measure described herein with respect to tracking the physiological phenomenon may similarly apply to tracking the presence of the compound.

Figure 3:
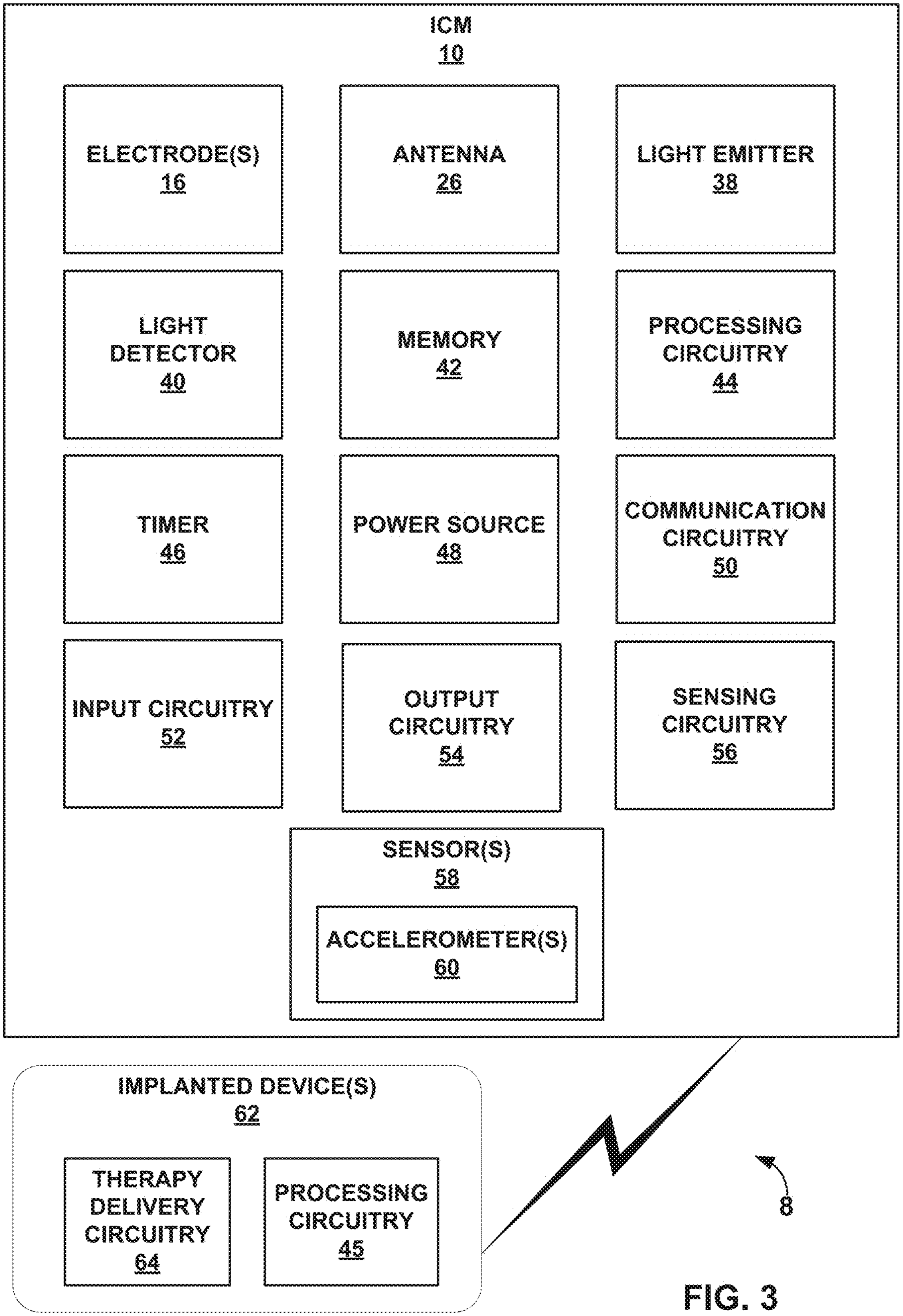
FIG. 3 is a block diagram of an example configuration of the system of FIG. 1 including an example of an implantable medical device that may be used to monitor one or more physiological parameters of a patient according to the present disclosure.

By using a user interface, such as described with respect to FIG. 3, dosing levels of the patient over time may be displayed and conveyed to the user. For example, the information displayed may be a simple measure or indication of when the medication was taken, or the information may be based on the detected dose in the blood or tissue. In an example, the displayed information may include a percentage of a period of time (e.g., a day, a week, a month) that the patient is at the dose. In an example, the displayed information may include a plot, such as a dose level trend plotted throughout the period of time. The user interface may display or provide a reminder to the patient to take medication, such as if the IMD determines that the patient has not taken a medication when the patient should have. The output circuitry may provide an indication to the user (e.g., the patient, the clinic, or a caregiver) that the dose was missed.

In some examples, one or more wavelengths may be used. For example, a second wavelength may be used to account for and take out the background noise (e.g., for normalization as described further herein). In an example, the light emitter may emit multiple wavelengths of light. In an example, one or more light emitters may be used. Multiple wavelengths may be used, in some examples, such as for monitoring more than one compound or medication.

For example, the IMD may emit a light signal (e.g., a first signal) using the light emitter. The light emitter may also be configured to emit a second light signal. The first signal may comprise a first wavelength configured to cause a first fluorescent marker to emit a fluoresced signal. The second light signal may comprise a second wavelength, and the processing circuitry may be configured to determine background noise associated with the second signal. In an example, the second signal may cause a second fluorescent marker administered into the patient to emit a second fluoresced signal. The processing circuitry may be configured to determine a characteristic of the second fluorescent marker based on the second signal and the second fluoresced signal. In some examples, more than two signals may be used. In this way background noise and characteristics of one or more fluorescent markers may be determined by the processing circuitry.

In an example, a second signal may be used to set a baseline (e.g., normalize) the first signal. Orally ingested drugs may be absorbed differently in the gut due to the conditions of the patient. Therefore, the concentration of a drug in the blood may vary, even when the dosage does not change. In an example, a drug pill may comprise a second fluorescent marker, where the second fluorescent maker is easily absorbable under most or all conditions. In some examples, any compound (e.g., the first marker or the second marker) may be embedded in the pill casing, within the pill, or within a compartment of the pill. As such, the processing circuitry may track a second fluoresced signal to normalize the first fluoresced signal corresponding to the drug. In this way, a baseline level against which the primary marker of interest may be determined. The processing circuitry may compare the baseline level to a metric based on the first fluoresced signal. If, for example, the baseline signal is stronger (e.g., twice as strong, or twice as bright) than the first fluoresced signal, then it may be known that only half of the first fluorescent marker corresponding to the first fluoresced signal, was absorbed. As such, the dosage may then be increased (e.g., by the physician or automatically via a drug pump) to compensate for this shortage.

By using the techniques described herein, using the second marker (e.g., where the second marker may not necessarily be affected by the physiologic phenomenon being tracked) that is easily absorbed in the gut may enable the calculation of how much of the first marker has been absorbed (e.g., processing circuitry may be configured to determine a percentage of the first marker that was absorbed, such as at a given time or over a period of time). In some examples, the IMD comprises the processing circuitry, and in other examples, an external device comprises such processing circuitry such that signals from the IMD are uploaded to the external device.

In some examples, the isobestic point and/or ratiometric techniques, as described further herein, may be used to normalize for absorption or other confounding factors, such as for the first fluorescent marker, the second fluorescent marker, or another compound. As such normalization of with a secondary compound may be implemented without necessarily requiring two fluorophores.

In an example, a first signal may be unique for a first compound (e.g., fluorescent marker), a second signal may be unique for a second compound, and a third signal may be configured to take out the background noise for the first and second signals. The IMD described herein may provide enhanced patient medication compliance monitoring by tracking multiple drugs at once, such as by tracking multiple tracers.

The systems and techniques described herein include a drug compliance monitor that may be linked to one or more implanted sensors, one or more external sensors, or a combination thereof, such as may be configured to monitor a fluid state of the patient, arrhythmia, pulmonary artery pressure, or blood pressure. In an example where the sensors monitor for heart failure, a medical system may determine that the patient is at risk of an acute heart failure event, such as via measurements taken with the sensors. In an example, in response to the determination, the medical system may initiate or change a therapy. In some examples, the medical system may inform the clinician to initiate or change a therapy including based on the tailored dosage described above. In an example, in response to the determination, the medical system may inform a clinician to initiate or change a therapy. In some examples, the sensors used to monitor the patient may be used to monitor the effects of the therapy.

For example, the medical system described herein may be used to provide guidance for patient care. The medical system may detect a heart failure event in a patient, then determine if the patient has been compliant by taking their medications (e.g., a diuretic). If the patient has been compliant, then the medical system may direct the patient to change a dosage of a medication, for example, the diuretic, and the medical system may monitor, such as via sensors described herein, the results of the change in medication (e.g., improvement, stability, or worsening of heart failure). Then, based on the results of the change in medication, the medical system may provide further therapy or may provide information to the clinician.

As such, the IMD or system may monitor a first physiological phenomenon of the patient, such as a physiological phenomenon relating to (e.g., resulting from) compliance with a medication regimen. The IMD may monitor a second physiological phenomenon of the patient, such as relating to another state of the patient (e.g., the heart failure event, chronic obstructive pulmonary disease (COPD), hypertension, or state). The IMD may detect a worsening state of the patient, such as by monitoring the second physiological condition. For example, the processing circuitry may be configured to detect that the second physiological phenomenon meets a criterion (e.g., such as a critical health metric, which may be one or more of a heart rate, heart rate variability, respiration index, fluid status, temperature, or other health metric of the patient), and the processing circuitry may be configured to determine whether the patient is compliant with the medication regimen. The processing circuitry may determine the patient's compliance, for example, based on the characteristic of the fluorescent marker, such as may include a corresponding metabolism profile to the medication at issue. The processing circuitry may compare the medications taken based on the tracked characteristic of the fluorescent marker to the medications prescribed (e.g., such as based on information stored in the memory of the IMD). In this way, the IMD may determine if the patient is compliant with the medication regimen. In response to the comparison, processing circuitry may determine an updated medication regimen or other therapy (e.g., an electrical stimulation therapy). In an example, the processing circuitry may determine the medication regimen based at least in part on the patient's compliance (e.g., based on a patient compliance indication). Throughout the process, the IMD may inform the clinician of the patient status, patient compliance, or modification of the treatment regimen, such as to allow for clinician approval at each step. The output circuitry may be configured to provide the patient compliance indication, such as based upon the determination that the second physiologic phenomenon meets the criterion and the determination of the patient's compliance. The output circuitry may be configured to provide information about the medication regimen and the patient's compliance with the medication regimen, such as to other devices in the system.

In some examples, the systems and techniques described herein include monitoring organ function of the patient. For example, a fluorescent tracer may be administered to the patient and the IMD may track the amount of tracer as it is absorbed or removed by the organ. The fluorescent tracer may have a known clearance profile, such as for an organ like the kidney or the liver, or a known absorption profile, such as by the gut. In some examples, the IMD determines the clearance or absorption profile. As such, the IMD may derive organ function, including by analyzing the tracer removal profile. Patients with chronic disease (e.g., chronic kidney disease (CKD), COPD, heart failure, liver disease, or other chronic disease), may need to monitor chronic organ function. The systems and techniques described herein may provide improved chronic monitoring of organ function, and may inform a user (e.g., a health care provider, a physician, a nurse, the patient, or another) or a medical device when there is a need to change a therapy. In an example, the medical system informs the user when a therapy needs to be stopped, such as when to stop a diuretic treatment. In an example, the medical system informs the user when a new therapy should be started. As such, the systems and techniques described herein may be beneficial for cases such as heart failure or CKD, where diuretics may be frequently given to the patient to remove fluid, but may ultimately cause damage to the kidneys. In some examples, the medical system described herein monitors organ function on a non-chronic basis. In some examples, the medical system described herein provides continuous monitoring, such as around an acute clinical event.

In an example, the physiological phenomenon may correspond to an organ absorption or an organ clearance of the fluorescent marker. In an example, the characteristic of the fluorescent marker may correspond to one of a respective organ absorption or respective organ clearance profile of the fluorescent marker. As such, the processing circuitry may be configured to determine a peak of the tracked characteristic of the fluorescent marker.

In an example, the processing circuitry may be configured to determine a value of the characteristic of the fluorescent marker, such as a concentration or amount at a time. In an example, the processing circuitry may be configured determine when the value of the characteristic of the fluorescent marker meets a threshold, such as peak in the amount of the fluorescent marker over a time window. Such a time window may correspond to a drug metabolism profile, or may be longer than the time it takes patient to metabolize the drug to capture data before the patient is administered the drug and through the time it takes the patient to fully process the drug. The processing circuitry may detect the presence of the peak amount of the tracer, such as to initiate the measuring of the decay of the tracer.

As described above, the fluorescent tracer may have a known clearance profile (e.g., rate of clearance), such as for an organ, or a known absorption profile. The processing circuitry, in some examples, may derive the clearance rate for an organ, or may derive the absorption profile. The processing circuitry may detect a point in time when the amount of the fluorescent marker is or is becoming too low to measure, and prompt the user to administer more of the fluorescent marker to the patient.

As such, the system may display trends in organ function throughout the day, or daily over weeks or months. Various tracers may be used for this organ function monitoring. In some examples, the tracer may be a compound that is directly cleared or metabolized by the target organ, such as creatinine that may be cleared by the kidney. In some examples, the tracer may be a compound that binds to another compound that may be removed or excreted (e.g., after drug intake) by the target organ, such as urea that may be removed by the kidney. By tracking the characteristic of the fluorescent marker using a relatively small IMD, as described herein, patient outcomes may be improved while maintaining patient comfort and minimizing the amount of devices the patient may need to interact with (e.g., be implanted with).

The systems and techniques described herein include biomarker monitoring. For example, the fluorescent tracer may be configured to bind to a biomarker or an injected substrate. In an example, the substrate may be formed on the housing (e.g., injected proximate to the housing or formed on the housing before implant). In instances where there may be a need to monitor for a biomarker, such as to track the progression of a disease or an acute event, the systems and techniques described herein may track a tracer that may, for example, bind to the biomarker of interest. An example of a biomarker of interest may include prostate-specific antigen (PSA) in the case of prostate cancer, creatinine in the case of kidney disease, B-type natriuretic peptide (BNP) in the case of heart failure, troponin in the case of heart attack or heart failure, molecular biomarkers of stroke, or other biomarkers such as for a cancer or another disease state, such as cancer cells, compounds produced by cancer cells, and/or compounds produced by immune response to cancer cells. In some examples, a system including the IMD may be configured to generate an alert (e.g., to the patient and/or a clinician) when the system determines that an amount or concentration of the biomarker satisfies or does not satisfy a threshold amount or concentration. In other examples, as further described below, a system including the IMD may be configured to alert the patient and/or clinician to the presence of the biomarker if the system determines the biomarker is present in any amount or concentration.

In an example, the IMD may comprise a Reveal LINQ™ ICM, available from Medtronic plc, of Dublin, Ireland. The patient may be implanted with the Reveal LINQ™ ICM or another IMD that is configured to carry out the techniques described herein. The IMD may be configured to chronically monitor the patient.

In some examples, the patient may be a cancer patient (e.g., a cancer survivor) or other patient who has or who has had a health condition that may be characterized by the presence of a biomarker within the patient's body. In such examples, the biomarker may be associated with a current or past health condition of the patient. As such, and as further described herein, the IMD may be configured to inform a user that a biomarker associated with the patient's current or past health condition is present (e.g., even a small amount). In some such examples, the biomarker may not be present, even at a low amount or concentration, in patients that do not have the patient's current or past health condition. Thus, in such examples, the IMD may be configured to inform the user that the biomarker is present if processing circuitry of a system including the IMD determines that any amount or concentration of the biomarker is present. In examples in which the patient has or has had cancer, a biomarker associated with the patient's current or past health condition may include a cancer cell, a compound produced by a cancer cell, and/or a compound produced by immune response to cancer cells. By chronically monitoring the patient using the improved systems described herein, serial testing of patients may be greatly reduced or even eliminated, for example, and may provide the capability to detect recurrence of a disease state such as cancer at the earliest state of such recurrence.

A biomarker may be present at a certain concentration in the blood of the patient at any given time. By administering the tracer (e.g., the fluorescent marker) that may be detected with the medical device as described herein, the medical device may provide an indication of the amount of biomarker present at a particular time, or over time, such as to track the progression of a disease state or determine an efficacy of treatment of a disease state. The biomarker may bind to the tracer. In some examples, a substrate may be injected over or near the target site (e.g., near the IMD) that may allow for competitive binding between the biomarker of interest and the tracer.

A protein may recognize the biomarker (e.g., the protein and the biomarker may selectively bind to each other). In addition, the fluorescent marker may be configured to bind to the same protein. As such, the biomarker and the fluorescent marker may compete to bind to the protein. Therefore, if there is a relatively higher concentration of biomarker, then a relatively less strong fluoresced signal will be detected.

In some examples, the protein may be foreign to the patient's body, and therefore may have a potential to evoke an immune response. The possibility of the protein evoking an immune response may be minimized by coupling (e.g., coating) the protein on a surface of the ICM, such as the housing of the ICM, rather than allowing the protein to circulate in the blood or tissues. In an example, the ICM may comprise a membrane positioned over the portion of the ICM to which the protein is coupled. Such a membrane may be configured to allow the biomarker and the fluorescent marker to pass through the membrane while keeping out cells that might trigger the immune response.

In some examples, the ICM described herein may comprise the substrate. The substrate may be positioned on the housing of the ICM. In some examples, the substrate is coupled to the housing of the ICM. The substrate may interact with the drug delivered to the patient, with a compound delivered with the drug, with a biomarker, or with other compounds. In some examples, the substrate comprises the biomarker, the fluorescent marker, another administered compound of interest, individually or any combination thereof. By including the substrate on the ICM, the compound may react with the substrate to change its fluorescent properties. The substrate may be configured within relatively small reservoirs that are periodically opened to reveal new substrate, such as to overcome limitations of biofouling or used up substrate. In some examples, the substrate may be revealed (e.g., exposed) passively over time, or may be revealed via control of a user.

The systems and techniques described herein may include a stable sensor system (e.g., a detecting assay) that may be suitably sterilized. For example, the systems and techniques may include an optical approach using fluorescence resonance energy transfer (FRET) assay, detecting binding events on surfaces (e.g., a bead) using plasmonic waves, conformal changes in proteins or aptamers, enzymatic degradation of biomarker, or detection of products thereof.

The IMD may be used to quantify a change in the fluorescence associated with the tracer. For example, a higher fluorescence may indicate there is relatively less of the biomarker of interest present and relatively more of the fluorescent marker bound to the substrate. For example, for an injected substrate that lasts on the order of weeks to months, then the medical system may track the presence or absence of myocardial damage with intermittent ischemic events (e.g., via troponin), changes in PSA with a cancer therapy regimen, or changes in kidney function with a diuretic drug (e.g., via creatinine).

The systems and techniques described herein include medication titration with organ function monitoring. For example, for a patient experiencing an acute decompensated heart failure event, clinicians may turn to administering different or higher doses of diuretics. However, such administration of diuretic may impair renal function. As such, the selection of an appropriate therapy may be influenced by the patient's acute renal function. In some instances, if the renal function is poor, then the clinician may be less aggressive with diuretic therapy. In instances where renal function starts to deteriorate, then the clinician may stop or change the diuretic therapy. As such, the systems and techniques described herein include determining renal function and monitoring renal function over a period of time (e.g., 7-10 days).

In some examples, the second physiological phenomenon, as described herein, may correspond to the heart failure event. The processing circuitry may be configured to determine the heart failure event based on monitoring cardiac activity of the patient, as described further herein. In general, the IMD described herein may detect the onset of an acute heart failure event and prompt a user to administer a tracer to the patient. For example, the IMD may prompt the patient to take a kidney function tracer. The IMD may determine kidney function based on tracking the kidney function tracer (e.g., processing circuitry may be configured to track a characteristic of the kidney function tracer, such as a fluorescent marker, in response to the patient's compliance with a medication instruction. The IMD may provide the medication instruction, which may include the dose and type of medication to be administered. The first physiological phenomenon, as descried herein, may correspond to kidney function of the patient, in some examples.

In some examples, the light emitter may emit a signal that may be reflected off a marker or other compound. The reflected signal may comprise a different wavelength (e.g., the emitted signal may have a first wavelength while the reflected signal may have a second wavelength). The emitted signal may reflect off of the marker (e.g., any compound described herein) and/or other compounds. The light detector may detect the reflected signal. The processing circuitry may determine a characteristic of the marker based on the emitted signal and/or the reflected signal. In some examples, processing circuitry may be configured to determine an amount of the marker present, such as based on the wavelength of the reflected signal, an amplitude of the reflected signal, or other characteristics of the reflected signal.

The characteristic of the marker may be indicative of a presence of a compound in the patient. The characteristic of the marker may include an amount of the compound, such as a measure over time. The reflected signal may be indicative of the presence or absence of the marker. In some examples, the compound may be a medication. In some examples, the marker may bind to a drug or a substrate, such as described herein.

In some examples, a characteristic of the reflected signal may change based on a condition of the marker. For example, the wavelength or amplitude of the reflected signal may change based the condition of the marker. The condition of the marker may include different states of the marker, such as whether the marker is bound to a drug or not, whether the marker is encased in a pill, or other states. The characteristic of the reflected signal may also be based on other markers or compounds present. For example, the emitted signal may reflect off more than one compound or tissue, and the light detector may be configured to detect the reflected signal. The processing circuitry may be configured to determine an amount of one or more compounds (e.g., the marker and the drug) from the reflected signal.

In some examples, where the light detector detects the reflected signal, the emitted signal may be reflected off compounds that occur naturally in the patient. In some examples, compounds are administered to the patient. In some examples, a marker or tracer may comprise particular properties (e.g., reflective properties), and the marker or tracer may be administered to the patient, although this may not be required. The processing circuitry may be configured to determine a characteristic of the marker or tracer, such as based on the reflective properties.

The output circuitry may be configured to provide the patient medication instruction, such as may correspond to an administration of a dose of the tracer. In some examples, the processing circuitry may be configured to track the characteristic of the tracer in response to the patient's compliance with the medication instruction.

In the examples described herein, any suitable fluorophore may be used (e.g., various types of dyes, proteins, or other molecules). For example, a suitable fluorophore may be capable of diffusing through a membrane of the gastrointestinal tract and into the bloodstream, such as a fluorophore that is substantially non-hydrophilic to traverse the membrane. Such a fluorophore may be administered orally instead of intravenously or subdermally, which may enable the patient to administer the fluorophore and/or better tolerate its administration. Example fluorophores having such characteristics may include betalain-class dyes made fluorescent as described above, or any other such fluorophores suitable for diffusion through a hydrophobic membrane.

FIG. 1 is a conceptual drawing illustrating an example medical system 8 (also may be referred to as a "medical system" or a "system") in conjunction with a patient 2. In general, systems (e.g., system 8) may include one or more medical devices, leads, implanted or external sensors, external devices, or other components configured for techniques described herein. Medical system 8 is an example of a medical device system configured to implement the techniques described herein for tracking a characteristic of a fluorescent marker and monitoring other physiological parameters of patient 2, such as may include a fluoresced signal, a characteristic of the fluorescent marker that is indicative of a physiological phenomenon of patient 2, cardiovascular pressure, blood pressure, body position or posture, patient motion, patient activity, or heart rate. In the illustrated example, medical system 8 includes an implantable medical device (IMD) 10 (also may be referred to as an implantable monitoring device, an implantable hub device, or an insertable cardiac monitor (ICM)), such as may be in communication with one or more external devices 12 or one or more other implanted devices, not shown. Such other implantable devices may be an implantable pacemaker, an implantable cardiac defibrillator, a cardiac resynchronization therapy (CRT) device (e.g., CRT-D defibrillator or CRT-P pacemaker), a neurostimulator, a nerve stimulator, a drug pump (e.g., an insulin pump), or other devices. In some examples, some of these devices may include the light emitter and light detector described herein. In some examples, some of these devices may alternatively be external medical devices, such as the insulin pump. In some examples another implantable device, also not shown, may include an implantable pressure sensing device that may be implanted within a pulmonary artery of heart 4. In some examples, pulmonary artery 6A of heart 4 may comprise a left pulmonary artery, and pulmonary artery 6B may comprise a right pulmonary artery.

In the example of FIG. 1, IMD 10 is an insertable cardiac monitor (ICM) capable of sensing and recording cardiac electrogram (EGM) signals from a position outside of heart 4 via electrodes, and will be referred to as ICM 10 hereafter. In some examples, ICM 10 includes or is coupled to one or more additional sensors, such as accelerometers, that generate one or more signals that vary based on patient motion or posture, blood flow, or respiration. ICM 10 may monitor a physiological parameter indicative of patient state, such as posture, heart rate, activity level, heart rate, or respiration rate, and ICM 10 may measure the one or more physiological parameters at times when another implantable medical device, not shown, is measuring cardiovascular pressure. In some examples, such physiological parameters may help enable processing circuitry of ICM 10 to determine one or more of an organ function, a compliance with a medication regimen, or a biomarker status (e.g., presence or level) of patient 2. ICM 10 may include a light emitter configured to emit a signal (e.g., a light signal) into a target site of patient 2. In an example, the target site includes the space around ICM 10 within patient 2. ICM 10 may include a light detector configured to detect a light signal, such as described further below.

ICM 10 may include processing circuitry configured to determine a characteristic of the fluorescent marker. In an example, the processing circuitry may be configured to track the characteristic of the fluorescent marker. In an example, the processing circuitry may be configured to determine the patient's compliance, such as with a medication regimen. In an example, the processing circuitry may be configured to determine a medication level in patient 2, such as may be based on information about the medication (e.g., an administration time, a dosage, a medication type, a medication metabolism profile, a medication history, or the like) and based on the characteristic of the marker. In tracking the characteristic of the marker over time, the processing circuitry may store the tracked information for use in determining, the medication level in patient 2.

In some examples, ICM 10 may be implanted outside of the thoracic cavity of patient 2 (e.g., subcutaneously or submuscularly, such as the pectoral location illustrated in FIG. 1). ICM 10 may be positioned near the sternum near or just below the level of heart 4. In some examples, ICM 10 may take the form of a Reveal LINQ™ ICM, available from Medtronic plc, of Dublin, Ireland.

ICM 10 may include a timer and processing circuitry configured to determine a time of day based on the timer value, or may determine the amount of time between events (e.g., administration of a medication to measurement of a characteristic of a fluorescent marker). ICM 10 may include wireless communication circuitry configured to transmit or receive a signal from another device, such as to or from one or more external devices 12, or to another implanted medical device, for example. ICM 10 may determine a patient's compliance with a medication regimen, transmit that determination to external device 12, which may include a user interface 66 to alert the user (e.g., patient 2 or a clinician) to take steps to ensure compliance. User interface 66 may include a display to present information to a user. In general, the user may interact with user interface 66. In some examples, user interface 66 comprises a keyboard, keypad, touch screen, mouse, or the like, for receiving input from the user. User interface 66 may include a light or speaker, such as may be used to provide an indication or alert to the user. Examples of user interface 66 include a computing device such as a tablet or mobile phone (e.g., a smart phone), which may be configured to communicate with ICM 10, such as to retrieve data and/or program operation of ICM 10 or other devices. Processing circuitry can control user interface 66, such as by using communication circuitry to, for example, initiate a blinking light or audible sound to alert the user of a risk of harm to the patient. In some examples, ICM 10 may transmit the determination to another medical device to provide therapy (e.g., such as a change in drug dosage).

ICM 10 may transmit data about the tracked characteristic of the fluorescent marker, and other physiological parameter data acquired by ICM 10, to external device 12. ICM 10 may also transmit cardiovascular pressure measurements, for example, received from another implanted sensor device, not shown, to external device 12, such as when ICM 10 is functioning as a hub device. For example, ICM 10 may transmit any data described herein related to cardiovascular pressure, posture, heart rate, activity level, respiration rate, or other physiological parameters to external device 12. For purposes of this disclosure, a characteristic of the fluorescent marker, the tracked characteristic of the fluorescent marker, or other physiological measurements may include one or more numerical values, multi-variable tables (e.g., such values as a function of time), or other techniques for storing such data.

External device 12 may be a computing device (e.g., used in a home, ambulatory, clinic, or hospital setting) to communicate with ICM 10 via wireless telemetry. External device 12 may include or be coupled to a remote patient monitoring system, such as Carelink®, available from Medtronic plc, of Dublin, Ireland. External device 12 may be, as an example, a programmer, external monitor, or a consumer device (e.g., a smart phone). In some examples, external device 12 may receive data, alerts, patient instructions, or other information from ICM 10.

External device 12 may be used to program commands or operating parameters into ICM 10 for controlling its functioning (e.g., when configured as a programmer for ICM 10). External device 12 may be used to interrogate ICM 10 to retrieve data, including device operational data as well as physiological data accumulated in IMD memory. The interrogation may be automatic, such as according to a schedule, or in response to a remote or local user command. Programmers, external monitors, and consumer devices are examples of external devices 12 that may be used to interrogate ICM 10. Examples of communication techniques used by ICM 10 and external device 12 include radiofrequency (RF) telemetry, which may be an RF link established via Bluetooth, WiFi, or medical implant communication service (MICS). In some examples, external device 12 includes processing circuitry. The processing circuitry of external device 12 may be configured to perform any of the techniques described with respect to processing circuitry 44, such as described further herein. In some examples, external device 12 includes user interface 66, described further below.

Medical system 8 is an example of a medical device system configured to track the characteristic of the fluorescent marker. The techniques described herein may be performed by processing circuitry of medical system 8, such as processing circuitry of one or more of ICM 10, external device 12, and one or more other implanted or external devices not shown, individually, or collectively. Examples of the one or more other implanted or external devices may include an external cardiac monitor, an external pacemaker, a cardioverter, a defibrillator, a blood analyzer, a breath analyzer, imaging machines, or a drug pump. The communication circuitry of each of the devices of system 8 allows the devices to communicate with one another.

Figure 2:
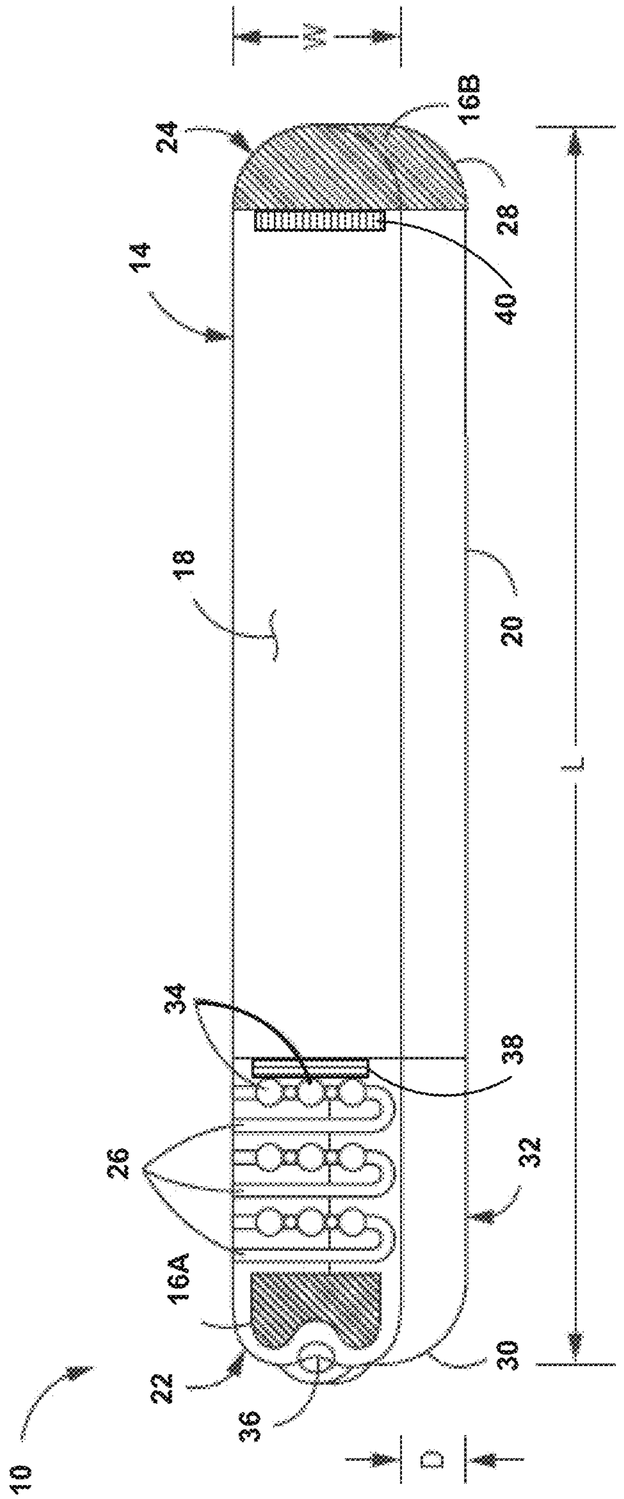
FIG. 2 is a conceptual drawing illustrating an example of a configuration of an implantable medical device.

FIG. 2 is a conceptual drawing illustrating an example of a configuration of ICM 10. In the example shown in FIG. 2, ICM 10 may be embodied as a monitoring device having housing 14, proximal electrode 16A and distal electrode 16B (individually or collectively "electrode 16" or "electrodes 16"). Housing 14 may further comprise first major surface 18, second major surface 20, proximal end 22, and distal end 24. Housing 14 encloses electronic circuitry located inside the ICM 10 and protects the circuitry contained therein from body fluids. Electrical feedthroughs provide electrical connection of electrodes 16. In an example, ICM 10 may be embodied as an external monitor, such as patch that may be positioned on an external surface of the patient, or another type of medical device (e.g., instead of as an ICM), such as described further herein.

In the example shown in FIG. 2, ICM 10 is defined by a length "L," a width "W," and thickness or depth "D." ICM 10 may be in the form of an elongated rectangular prism wherein the length L is significantly larger than the width W, which in turn is larger than the depth D. In one example, the geometry of the ICM 10—in particular, a width W being greater than the depth D—is selected to allow ICM 10 to be inserted under the skin of the patient using a minimally invasive procedure and to remain in the desired orientation during insertion. For example, the device shown in FIG. 2 includes radial asymmetries (notably, the rectangular shape) along the longitudinal axis that maintains the device in the proper orientation following insertion. For example, in one example the spacing between proximal electrode 16A and distal electrode 16B may range from thirty millimeters (mm) to fifty-five mm, thirty-five mm to fifty-five mm, and from forty mm to fifty-five mm and may be any range or individual spacing from twenty-five mm to sixty mm. In some examples, the length L may be from thirty mm to about seventy mm. In other examples, the length L may range from forty mm to sixty mm, forty-five mm to sixty mm and may be any length or range of lengths between about thirty mm and about seventy mm. In addition, the width W of first major surface 18 may range from three mm to ten mm and may be any single or range of widths between three mm and ten mm. The thickness of depth D of ICM 10 may range from two mm to nine mm. In other examples, the depth D of ICM 10 may range from two mm to five mm and may be any single or range of depths from two mm to nine mm. In addition, ICM 10 according to an example of the present disclosure is has a geometry and size designed for ease of implant and patient comfort. Examples of ICM 10 described in this disclosure may have a volume of three cubic centimeters (cm) or less, one-and-a-half cubic cm or less or any volume between three and one-and-a-half cubic centimeters. In addition, in the example shown in FIG. 2, proximal end 22 and distal end 24 are rounded to reduce discomfort and irritation to surrounding tissue once inserted under the skin of the patient. In some examples, ICM 10, including instrument and method for inserting ICM 10 is configured as described, for example, in U.S. Patent Application Publication No. 2014/0276928, incorporated herein by reference in its entirety. In some examples, ICM 10 is configured as described, for example, in U.S. Patent Application Publication No. 2016/0310031, incorporated herein by reference.

In the example shown in FIG. 2, once inserted within the patient, the first major surface 18 faces outward, toward the skin of the patient while the second major surface 20 is located opposite the first major surface 18. Consequently, the first and second major surfaces may face in directions along a sagittal axis of patient 2 (see FIG. 1), and this orientation may be consistently achieved upon implantation due to the dimensions of ICM 10. Additionally, an accelerometer, or axis of an accelerometer, may be oriented along the sagittal axis.

Proximal electrode 16A and distal electrode 16B are used to sense cardiac signals (e.g., electrocardiogram (ECG) signals, intra-thoracically or extra-thoracically) which may be submuscularly or subcutaneously. ECG signals may be stored in a memory of the ICM 10, and ECG data may be transmitted via integrated antenna 26 to another medical device, which may be another implantable device or an external device, such as external device 12. In some examples, electrodes 16A and 16B may additionally or alternatively be used for sensing any bio-potential signal of interest, such as an intracardiac electrogram (EGM), electroencephalogram (EEG), electromyogram (EMG), or a nerve signal, from any implanted location.

In the example shown in FIG. 2, proximal electrode 16A is in close proximity to the proximal end 22, and distal electrode 16B is in close proximity to distal end 24. In this example, distal electrode 16B is not limited to a flattened, outward facing surface, but may extend from first major surface 18 around rounded edges 28 or end surface 30 and onto the second major surface 20 so that the electrode 16B has a three-dimensional curved configuration. In the example shown in FIG. 2, proximal electrode 16A is located on first major surface 18 and is substantially flat, outward facing. However, in other examples proximal electrode 16A may utilize the three-dimensional curved configuration of distal electrode 16B, providing a three-dimensional proximal electrode (not shown in this example). Similarly, in other examples distal electrode 16B may utilize a substantially flat, outward facing electrode located on first major surface 18 similar to that shown with respect to proximal electrode 16A. The various electrode configurations allow for configurations in which proximal electrode 16A and distal electrode 16B are located on both first major surface 18 and second major surface 20. In other configurations, such as that shown in FIG. 2, only one of proximal electrode 16A and distal electrode 16B is located on both major surfaces 18 and 20, and in still other configurations both proximal electrode 16A and distal electrode 16B are located on one of the first major surface 18 or the second major surface 20 (e.g., proximal electrode 16A located on first major surface 18 while distal electrode 16B is located on second major surface 20). In another example, ICM 10 may include electrodes 16 on both first major surface 18 and second major surface 20 at or near the proximal and distal ends of the device, such that a total of four electrodes 16 are included on ICM 10. Electrodes 16 may be formed of a plurality of different types of biocompatible conductive material (e.g., stainless steel, titanium, platinum, iridium, or alloys thereof), and may utilize one or more coatings such as titanium nitride or fractal titanium nitride.

In the example shown in FIG. 2, proximal end 22 includes a header assembly 32 that includes one or more of proximal electrode 16A, integrated antenna 26, anti-migration projections 34, or suture hole 36. Integrated antenna 26 is located on the same major surface (i.e., first major surface 18) as proximal electrode 16A and is also included as part of header assembly 32. Integrated antenna 26 allows ICM 10 to transmit or receive data. In other examples, integrated antenna 26 may be formed on the opposite major surface as proximal electrode 16A, or may be incorporated within the housing 14 of ICM 10. In the example shown in FIG. 2, anti-migration projections 34 are located adjacent to integrated antenna 26 and protrude away from first major surface 18 to prevent longitudinal movement of the device. In the example shown in FIG. 2 anti-migration projections 34 includes a plurality (e.g., six or nine) small bumps or protrusions extending away from first major surface 18. As discussed above, in other examples anti-migration projections 34 may be located on the opposite major surface as proximal electrode 16A or integrated antenna 26. In addition, in the example shown in FIG. 2 header assembly 32 includes suture hole 36, which provides another means of securing ICM 10 to the patient to prevent movement following insert. In the example shown, suture hole 36 is located adjacent to proximal electrode 16A. In one example, header assembly 32 is a molded header assembly made from a polymeric or plastic material, which may be integrated or separable from the main portion of ICM 10.

In the example shown in FIG. 2, ICM 10 includes a light emitter 38 and a light detector 40. As shown in FIG. 2, header assembly 32 may include light emitter 38, although, in other examples, header assembly may additionally or alternatively include light detector 40. Either or both of light emitter 38 or light detector 40 may be positioned on a medial section of ICM 10, such as part way between proximal end 22 and distal end 24, on either of major surfaces 18 or 20, or anywhere else on ICM 10 to achieve the techniques described herein. In an example, light emitter 38 and/or light detector 40 are on an opposite surface of ICM 10 as electrode 16A. In an example, light emitter 38 and/or light detector 40 are configured on ICM 10 to face out (e.g., towards the cutaneous tissue of the patient. In another example, light emitter 38 and/or light detector 40 are configured on ICM 10 to face in (e.g., toward the muscle of the patient).

Light emitter 38 may be configured to emit light into a target site of patient 2. In some examples, the target site may generally include the interstitial space around ICM 10 when ICM 10 is implanted in patient 2. Light emitter 38 may emit light directionally in that light emitter may direct the signal to a side of ICM 10, such as when light emitter 38 is disposed on the side of ICM 10 that includes first major surface 18. The target site may include a particular muscle or organ, a vascular structure, or any other physiological space or structure. In an example, light emitter 38 may deliver 180-degree light signals, such as 180 degrees along a dimension parallel to a longitudinal axis of ICM 10. In some examples, the light signal may be a cloud of light generally directed outward, toward the skin, such as described above, or the opposite direction. In some examples, the light signal may take the mean free path, as the light signal may be non-directional once emitted from light emitter 38. Light detector 40 may include a sapphire window, and may detect light, such from a fluoresced signal of a fluorescent marker in the target site as described herein. In some examples, ICM 10 includes a sapphire window, such as described with respect to FIG. 4B. In other examples, ICM 10 includes a glass material for the window, such as described further below.

In an example, either or both of light emitter 38 or light detector 40 may be disposed on a lead (e.g., a distal end of a medical lead), and the techniques described herein may be carried out using the lead in addition to or instead of a device such as ICM 10. Although chiefly described with respect to ICM 10, the systems and techniques described herein may be used with other devices (e.g., the lead, an external patch, or another device). An external patch may be affixed to the patient, such as by an adhesive. The patient may wear the patch, which may include one or more components described with respect to FIG. 3. For example, the patch may include a light emitter and a light detector, which may be arranged in a manner similar to that in which light emitter 38, light detector 40, and/or other sensors may be arranged on ICM 10. In an example, the patch is configured such that the light emitter and light detector face the skin of the patient when the patch is positioned on a surface of the skin of the patient. In some examples, signals emitted or received by one or more of the light emitter, light detector, and/or other sensors of a system including a medical device may be positioned such that the signal(s) at least partially penetrate the patient's skin (e.g., percutaneous placement) while the device (e.g., patch) remains external to the skin. In some examples in which one or more of a light emitter, a light detector, and/or other sensors of the system are positioned percutaneously and/or on the patient's skin, the external device may not necessarily be attached to the patient, but instead may be positioned with the patient remotely from the patient's skin, or with a clinician or other user. In a situation where the clinician desires to begin or change a drug therapy, for example, the kidney function of the patient may be monitored (e.g., for 7 to 10 days after the beginning or the change in the drug therapy). The patient may put the patch on himself or herself, or the patch may be affixed to the patient by a health care professional. The sensors positioned on such a patch may face toward the skin (e.g., in contrast to ICM 10, in which the sensors face up toward the skin).

FIG. 3 is a block diagram of an example of medical system 8 including an implantable monitoring device (e.g., an example of ICM 10 of FIG. 2) that may be used to track the characteristic of the fluorescent marker, or monitor one or more physiological parameters of a patient according to the present disclosure. In an example, system 8 may include one or more internal or implanted devices 62, which may include therapy delivery circuitry 64 or a processing circuitry (e.g., processing circuitry 44 or similar), as described further below. In an example, ICM 10 may include one or more electrodes 16, which may correspond to electrodes 16 described with respect to FIG. 1. In an example, ICM 10 may include antenna 26, light emitter 38, and light detector 40, which may correspond to the same elements described with respect to FIG. 1. In some examples, ICM 10 may include one or more light emitters. In some examples, ICM 10 may include one or more light detectors. For example, a first light detector may be placed on a first location on ICM 10 (e.g., relatively closer to proximal end 22), and a second light detector may be placed on a second location on ICM 10 (e.g., relatively closer to distal end 24). In some examples, the light emitter may comprise emission circuitry. In some examples, the light detector may comprise detection circuitry. The light emitter may further comprise a light source or an optical transmitter, and may be configured to generate an optical signal. The light detector may further comprise an optical receiver, and may be configured to detect an optical signal that has, for example, propagated through a target site of the patient. The emitted light signal may be absorbed by a marker (e.g., a fluorescent molecule), tissue, blood, or other material in the target site. The marker may emit light at a different, e.g., longer, wavelength than the emitted signal. An example of a light detector and a light emitter may include a PIN (p-type/intrinsic/n-type) photodiode detector and a light-emitting diode.

In an example, ICM 10 includes processing circuitry 44 and an associated memory 42. In some examples, ICM may include timer 46, power source 48, communication circuitry 50, input circuitry 52, output circuitry 54, or sensing circuitry 56. In an example, ICM includes one or more sensors 58, such as may include one or more accelerometers 60 or other sensors. However, an ICM 10 may need not include all of these components, or may include additional components. For example, ICM 10 may not include accelerometers 60 in some examples.

Memory 42 includes computer-readable instructions that, when executed by processing circuitry 44, cause ICM 10 and processing circuitry 44 to perform various functions attributed to ICM 10 and processing circuitry 44 herein (e.g., tracking the characteristic of the fluorescent marker). Memory 42 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. In some examples, memory 42 accumulates data, such as relating to the characteristic of the fluorescent marker or physiological data or relating to information sensed by sensors 58.

Processing circuitry 44 may perform the techniques described herein for tracking the characteristic of the fluorescent marker in the patient. Processing circuitry 44 may include fixed function circuitry, programmable processing circuitry, or both. Processing circuitry 44 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 44 may include multiple components, such as any combination of one or more microprocessors, one or more controllers, one or more DSPs, one or more ASICs, or one or more FPGAs, as well as other discrete or integrated logic circuitry. The functions attributed to processing circuitry 44 herein may be embodied as software, firmware, hardware or any combination thereof.

Sensing circuitry 56 may monitor signals from a selected two or more of electrodes 16 in order to monitor electrical activity of heart, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 56 may include one or more filters and amplifiers for filtering and amplifying a signal received from electrodes 16. In some examples, sensing circuitry 56 may sense or detect physiological parameters, such as heart rate, blood pressure, respiration, and the like.

The resulting cardiac electrical signal may be passed to cardiac event detection circuitry that detects a cardiac event when the cardiac electrical signal crosses a sensing threshold. The cardiac event detection circuitry may include a rectifier, filter or amplifier, a sense amplifier, comparator, or analog-to-digital converter. Sensing circuitry 56 outputs an indication to processing circuitry 44 in response to sensing of a cardiac event (e.g., detected P-waves or R-waves).

In this manner, processing circuitry 44 may receive detected cardiac event signals corresponding to the occurrence of detected R-waves and P-waves in the respective chambers of heart. Indications of detected R-waves and P-waves may be used for detecting ventricular or atrial tachyarrhythmia episodes, e.g., ventricular or atrial fibrillation episodes. Some detection channels may be configured to detect cardiac events, such as P- or R-waves, and provide indications of the occurrences of such events to processing circuitry 44, such as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 56 may also include switching circuitry to select which of the available electrodes 16 (or electrode polarities) are used to sense the heart activity. In examples with several electrodes 16, processing circuitry 44 may select the electrodes that function as sense electrodes (e.g., select the sensing configuration, via the switch module within sensing circuitry 56). Sensing circuitry 56 may also pass one or more digitized EGM signals to processing circuitry 44 for analysis (e.g., for use in cardiac rhythm discrimination).

In the example of FIG. 3, ICM 10 includes one or more sensors 58 that may be coupled to sensing circuitry 56. Although illustrated in FIG. 3 as included within ICM 10, one or more of sensors 58 may be external to ICM 10 (e.g., coupled to ICM 10 via one or more leads, or configured to wirelessly communicate with ICM 10). In some examples, sensors 58 transduce a signal indicative of physiological phenomenon of a patient, which may be amplified, filtered, or otherwise processed by sensing circuitry 56. In such examples, processing circuitry 44 determines values of physiological phenomenon of the patient based on the signals, and may communicate them (e.g., via a wired or wireless connection, to processing circuitry of an external device).

In some examples, sensors 58 include one or more accelerometers 60 (e.g., one or more three-axis accelerometers). Signals generated by the one or more accelerometers 60 may be indicative of, as examples, gross body movement (e.g., activity) of the patient, patient posture, heart sounds or other vibrations or movement associated with the beating of the heart, or coughing, rales, or other respiration abnormalities. Accelerometers 60 may produce and transmit signals to processing circuitry 44 for a determination as to whether the patient is in a target posture during a measurement of cardiovascular pressure by a pressure sensing device. In some examples, sensors 58 include one or more microphones configured to detect heart sounds or respiration abnormalities, or other sensors configured to detect patient activity or posture, such as gyroscopes or strain gauges. In some examples, sensors 58 may include sensors configured to transduce signals indicative of blood flow, oxygen saturation of blood, or patient temperature, and processing circuitry 44 may determine patient parameters values based on these signals. Sensors 58 may gather data that includes numerical values or waveforms of patient parameters. In some examples, sensors 58 may sense a waveform of a patient's cardiovascular pressure. Data indicating the waveform may be stored in memory 42 and transmitted to another device through communication circuitry 50. In some examples, ICM 10 may include a power source 48, which may be a rechargeable or non-rechargeable battery, or another suitable source of power.

System 8, as described herein, may include one or more implanted devices 62. In some examples, one or more implanted device(s) 62 (e.g., an IMD) may include processing circuitry 45. In an example, processing circuitry 45 of implanted device 62 may be configured to perform any of the techniques described with respect to processing circuitry 44 of ICD 10. For example, implanted device 62 may include therapy delivery circuitry 64. Therapy delivery circuitry 64 may be configured to generate and deliver electrical therapy to the heart, deliver drugs, or another therapy. Therapy delivery circuitry 64 may include one or more pulse generators, capacitors, or other components capable of generating or storing energy to deliver as pacing therapy, defibrillation therapy, cardioversion therapy, other therapy, or a combination of therapies. In some instances, therapy delivery circuitry 64 may include a first set of components configured to provide pacing therapy and a second set of components configured to provide anti-tachyarrhythmia shock therapy. In other instances, therapy delivery circuitry 64 may utilize the same set of components to provide both pacing and anti-tachyarrhythmia shock therapy. In still other instances, therapy delivery circuitry 64 may share some of the pacing and shock therapy components while using other components solely for pacing or shock delivery.

Therapy delivery circuitry 64 may include charging circuitry, one or more charge storage devices, such as one or more capacitors, and switching circuitry (not shown) that may be configured to control the capacitor(s) to discharge to electrodes that are coupled to therapy delivery circuitry 64 and control the widths of pulses. Charging of capacitors to a programmed pulse amplitude and discharging of the capacitors for a programmed pulse width may be performed by therapy delivery circuitry 64 according to control signals received from processing circuitry 44 or from processing circuitry apart of implanted device 62, which are provided by such processing circuitry according to parameters stored in memory 42. Processing circuitry 44 may control therapy delivery circuitry 64 to deliver the generated therapy to the heart via one or more combinations of electrodes apart of the IMD (e.g., according to parameters stored in memory 42). Therapy delivery circuitry 164 may include switch circuitry to select which of the available the electrodes that are used to deliver the therapy (e.g., as controlled by processing circuitry 44).

Communication circuitry 50 includes any suitable hardware, firmware, software or any combination thereof for communicating with another device, such as an external device 12 or implanted device 62 (e.g., another IMD or sensor). Under the control of processing circuitry 44, communication circuitry 50 may receive downlink telemetry from and send uplink telemetry to any implanted 62 or another device (e.g., external device 12) with the aid of an antenna, which may be internal or external. In some examples, communication circuitry 50 may communicate with a local external device (e.g., external device 12), and processing circuitry 44 may communicate with a networked computing device via the local external device and a computer network.

A clinician or other user may retrieve data from ICM 10 using implanted device 62 or another local or networked computing device configured to communicate with processing circuitry 44 via communication circuitry 50. The clinician may also program parameters of ICM 10 using implanted device 62 or another local or networked computing device. Although not illustrated in FIG. 3, communication circuitry 50 may be coupled or coupleable to electrodes 16, such as for tissue conductance communication (TCC) via electrodes 16.

Timer 46 may function with processing circuitry 44 to allow for continuous, intermittent, or periodic monitoring, which may include tracking regular intervals or irregular intervals of time. In other examples, monitoring using ICM 10 as described herein may occur in response to an event. ICM 10 may track in any way described above for any time period. For example, ICM 10 may track the marker for a time that includes a metabolism profile of a particular drug (e.g., if a drug takes 10 hours to be metabolized, then the monitoring time window may include at least 10 hours, such as 12 hours. As described herein, signal collection using ICM 10 may be sampled continuously or using pulsing of light or pulsing of detection based on a temporal schedule that may be chronological or triggered by other factors, such as another physiological trigger and/or one or more properties of the marker, such as a half-life. In some examples, the techniques described here may be performed by one or more processors, such as the processor of external device 12, implanted device 62, and processing circuitry 44. ICM 10 may be configured to sense the fluoresced signal, and the techniques for tracking the characteristic of the fluorescent marker may be performed by the one or more processors.

Figure 4A:
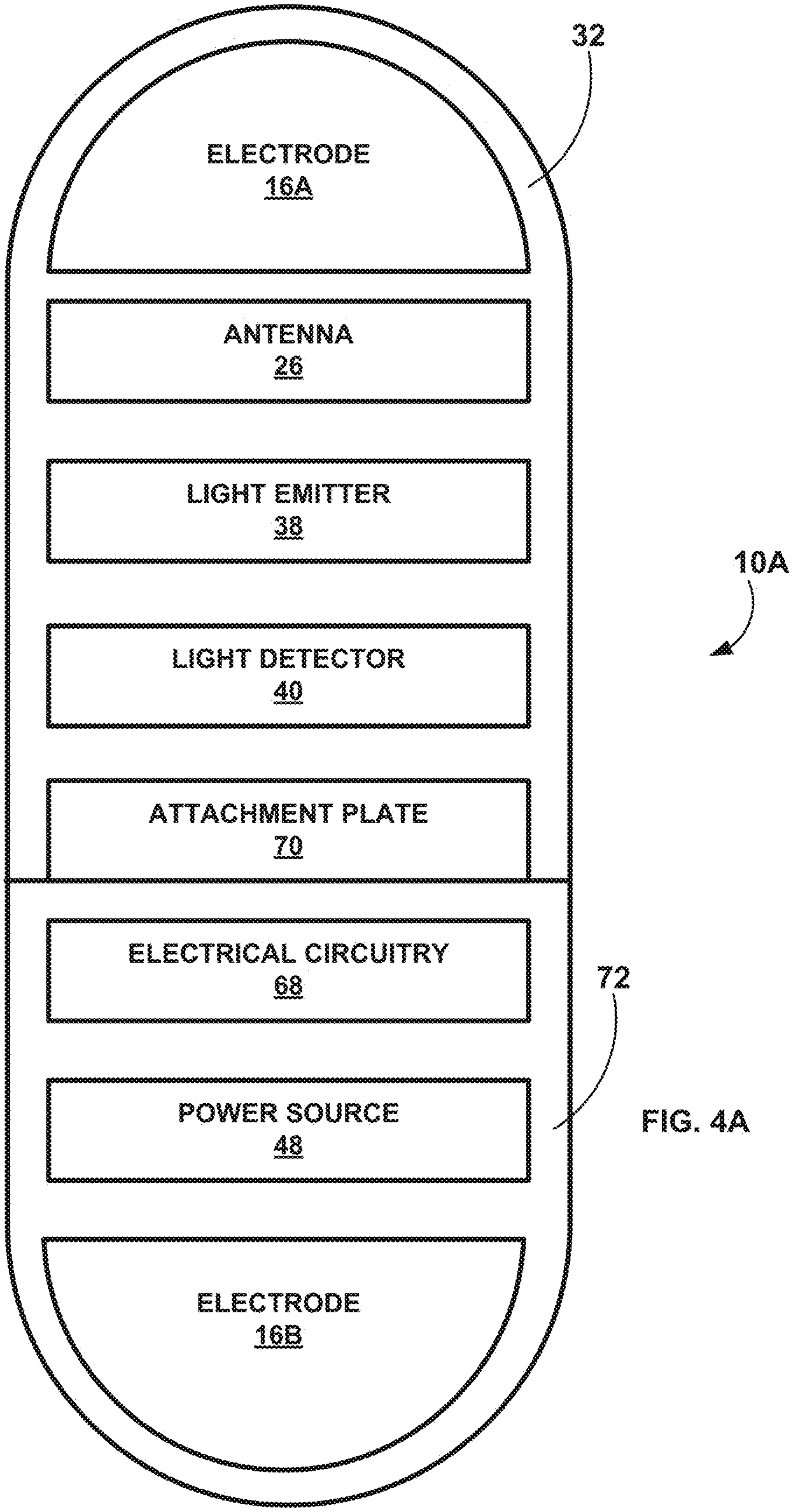
FIGS. 4A-4C are block diagrams of example configurations of implantable medical devices.

FIG. 4A is a functional block diagram of an example of ICM 10A that may be used to track a characteristic of a fluorescent marker or monitor one or more physiological parameters of a patient according to the present disclosure. Accordingly, all of the dimensions and physical characteristics described above for the embodiment of FIG. 2 may also apply to the embodiment shown in FIG. 4A and may also apply to the embodiment shown in FIG. 4B. As illustrated in FIG. 4A, ICM 10A may include header assembly 32 coupled to body portion 72 (the figures herein may not be to scale). In this example, header assembly 32 may include proximal electrode 16A, antenna 26, light emitter 38, light detector 40, and attachment plate 70. In some examples, proximal electrode 16A, antenna 26, light emitter 38, light detector 40, and attachment plate 70 may be molded into header assembly 32 via a molding process. In some examples, light emitter 38 and light detector 40 may be attached to ICM 10A after the molding process. Body portion 72 may include electrical circuitry 68 and power source 48, in some examples, which may be contained within a hermetic housing or can (e.g., formed of titanium or ceramic). Electrical circuitry 68 may be coupled to proximal electrode 16A and distal electrode 16B to sense cardiac signals and monitor events, including detecting premature ventricular contractions as described in more detail below. Electrical circuitry 68 may be coupled to light emitter 38 and light detector 40 to detect a fluoresced signal, such as described herein. Electrical circuitry 68 may also be connected to transmit and receive communications via antenna 26. Power source 48 provides power to electrical circuitry 68, as well as to any other components that require power. Power source 48 may include one or more energy storage devices, such as one or more rechargeable or non-rechargeable batteries.

Although not shown, electrical circuitry 68 may include any discrete or integrated electronic circuit components that implement analog or digital circuits capable of producing the functions described for tracking one or more characteristics of one or more fluorescent markers over time. For example, the electrical circuitry 68 may include analog circuits (e.g., pre-amplification circuits, filtering circuits, or other analog signal conditioning circuits). The modules may also include digital circuits (e.g., digital filters, combinational or sequential logic circuits, state machines, integrated circuits, a processor (e.g., shared, dedicated, or group)), that executes one or more software or firmware programs, memory devices, or any other suitable components or combination thereof that provide the described functionality.

Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth, WiFi, or other proprietary or non-proprietary wireless telemetry communication schemes. Antenna 26 may be coupled to electrical circuitry 68, which may drive antenna 26 to transmit signals to the programmer, and may receive signals received from the programmer via antenna 26. Attachment plate 70 may be configured to mechanically couple header 32 to body portion 72 of ICM 10A.

In the example shown in FIG. 4A, body portion 72 of ICM 10A may be configured to house electrical circuitry 68 and power source 48. In an example, body portion 72 may be formed of titanium or other biocompatible materials. Electrical circuitry 68 may comprise one or more electrical circuits configured to perform any function of ICM 10A. In an example, electrical circuitry 68 may include memory 42, processing circuitry 44, timer 46, communication circuitry 50, input circuitry 52, output circuitry 54, sensing circuitry 56, or other types of circuitry.

In some examples, the electrodes 16 are disposed on a first side of ICM 10A, and the light emitter 38 and light detector 40 are disposed on a second side of ICM 10A. In some examples, the first side may refer to first major surface 18 illustrated in FIG. 2 while the second side may refer to second major surface 20 illustrated in FIG. 2. In other examples, the first side may refer to proximal end 22 while the second side may refer to distal end 24. The first and second sides may refer to other sections of ICM 10A.

Figure 4B:
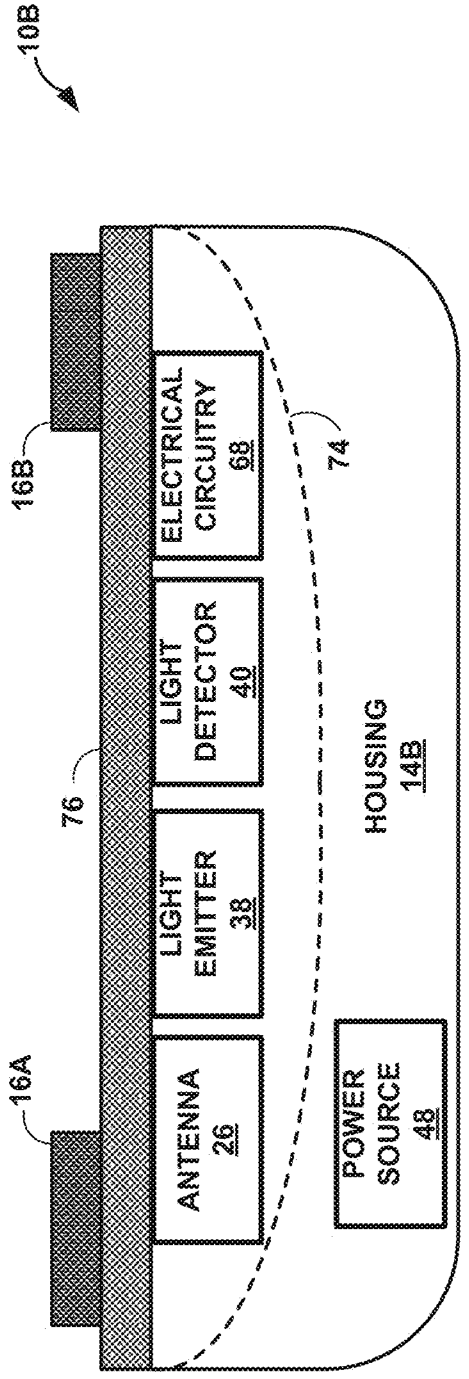

FIG. 4B is a functional block diagram of an example of ICM 10B that may be used to track a characteristic of a fluorescent marker or monitor one or more physiological parameters of a patient according to the present disclosure. ICM 10B may include insulative cover 76 and housing 14B, which may act as an elongate housing that includes antenna 26, light emitter 38, light detector 40, power source.

FIG. 4B depicts each electrodes 16A and 16B as being formed or placed above or on top of insulative cover 76. Although shown as shaded blocks, electrodes 16A and 16B may be included in ICM 10B in a similar manner as the examples of FIG. 2 or 4A, in some examples.

ICM 10B may include a wafer-scale insulative cover 76 positioned over a housing 14B to form the ICM. Electrical circuitry 68 (e.g., processing circuitry, sensing circuitry, communication circuitry, and/or other types of circuitry) may be formed on insulative cover 76, such as by using flip-chip technology. For example, antenna 26, light emitter 38, light detector 40, and/or electrical circuitry 68 may be formed on a side of insulative cover 76, and insulative cover 76 may be flipped onto housing 14B. When flipped and placed onto housing 14B, the circuitry and other components may be positioned on the bottom side of insulative cover 76 in a gap 74 defined by housing 14B. The electrical circuitry 68 on insulative cover 76 may be electrically connected to electrodes 16A and 16B through vias (not shown) formed through insulative cover 76. Insulative cover 76 may include additional vias. A portion or all of insulative cover 76 is transparent to the emitted and detected wavelengths. Insulative cover 76 may be formed of sapphire and/or any other suitable insulating material. Housing 14B may be formed from titanium or any other suitable material (e.g., a biocompatible material).

In some examples, insulative cover 76 may be sapphire and have a thickness of approximately three hundred micrometers (μM) to six hundred μM. Housing 14B may be titanium and have a thickness of approximately two hundred μM to five hundred PM. In an example, insulative cover 76 may be a glass material. In some examples, insulative cover 76 includes a parylene coating. These materials and dimensions are examples only, and other materials and other thicknesses are possible for devices of this disclosure.

In some examples, light emitter 38 may include an optical filter between light emitter 38 and insulative cover 76. In such examples, the optical filter may limit the spectrum of emitted light to be within a narrow band of wavelengths. Similarly, light detector 40 may include an optical filter between light detector 40 and insulative cover 76 so that light detector 40 detects light from a narrow spectrum, generally at longer wavelengths than the emitted spectrum. Other optical elements that may be included in the ICM 10B are index matching layers or antireflective coatings and an optical barrier that blocks light emitted sideways by the light emitter 38, preventing it from reaching light detector 40.

Sapphire may have a relatively larger index of refraction mismatch with the interior contents. Sapphire may have a more moderate mismatch with the surrounding tissue, such as when insulative cover 76 is a sapphire cover having a parylene coating. Such a mismatch may cause some light reflection of about 5% at each interface. Sapphire may be greater than 80% transmissive for wavelengths in the range of about 300 nm to about 4000 nm, and may have a relatively flat profile. In the case of variation, different transmissions at different wavelengths may be compensated for, such as using a ratiometric approach. Because sapphire is highly refractory, it is unlikely that its optical properties (e.g., absorption) change over time. In an example, optical properties of a parylene coating may change over time, such as at a relatively slow rate in comparison to the measurement time frames used for the techniques and systems described herein. In some examples, ICM 10B may include one or more transparent windows, one or more optical filters, other photodetectors, or other like components.

In some examples, light emitter 38 and light detector 40 are formed on (e.g., on top of, and outside housing 14B) insulative surface 76. Electrodes 16A and 16B may be positioned on ICM 10B in any manner, such as for example, described with respect to FIG. 2 above.

In an example, portions of ICM 10B is constructed in a similar manner as ICM 10A.

Figure 4C:
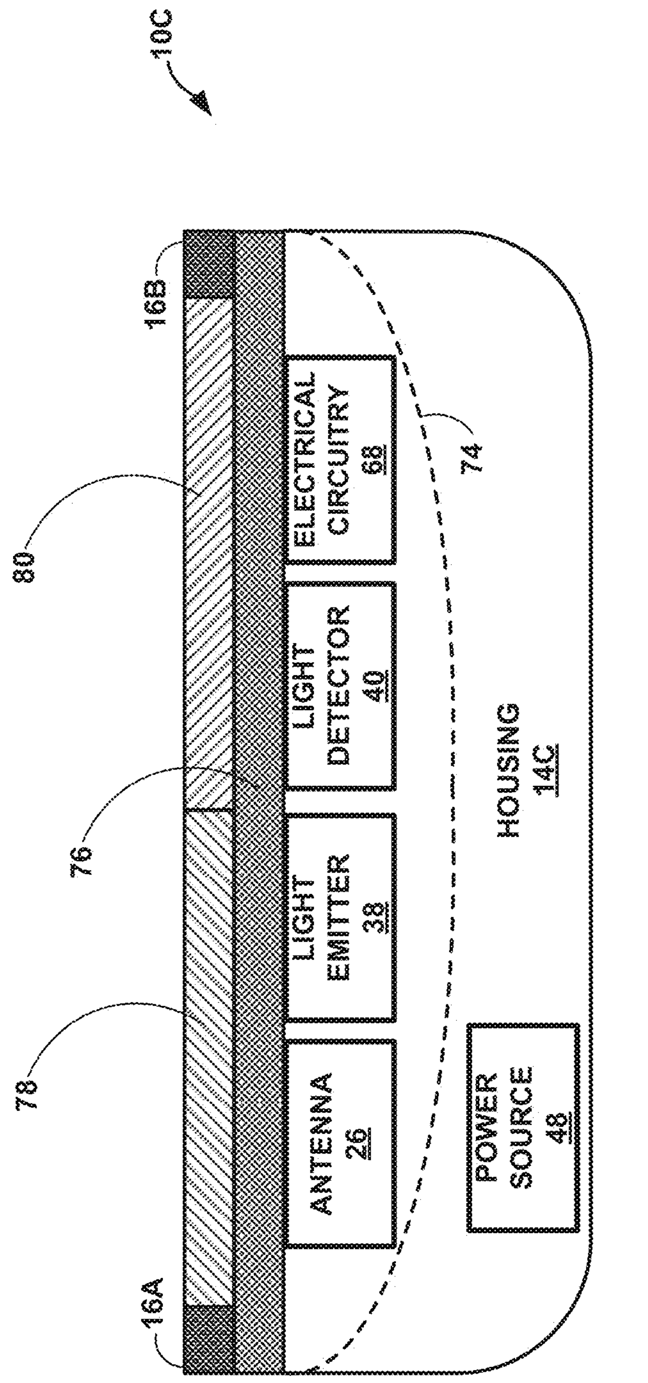

FIG. 4C is a functional block diagram of an example of ICM 10C that may be used to track a characteristic of a fluorescent marker or monitor one or more physiological parameters of a patient according to the present disclosure. ICM 10C may include the elements described with respect to ICM 10B. ICM 10C may comprise substrate 78 and/or one or more reservoirs 80. In some examples, as described above, substrate 78 may be positioned on housing 14C. The substrate may interact with the drug delivered to the patient, with a compound delivered with the drug, with a biomarker, or with other compounds. The substrate may comprise the biomarker, the fluorescent marker, another administered compound of interest, individually or any combination thereof, such as described above. Although shown with one reservoir 80 in FIG. 4C, ICM 10C may comprise multiple reservoirs 80 (e.g., two, five, ten, twenty, forty, or another number or reservoirs). Each reservoir 80 may be configured to house a relatively small amount of substrate 80. For example, in an embodiment with multiple reservoirs, the reservoirs 80 may be configured to periodically open to reveal the substrate 78. In some examples, ICM 10C comprises substrate 78 but not reservoirs 80, and substrate 78 may be positioned on or otherwise coupled to housing 14C. In some examples, ICM 10C comprises substrate 78 and reservoirs 80.

Figure 5:
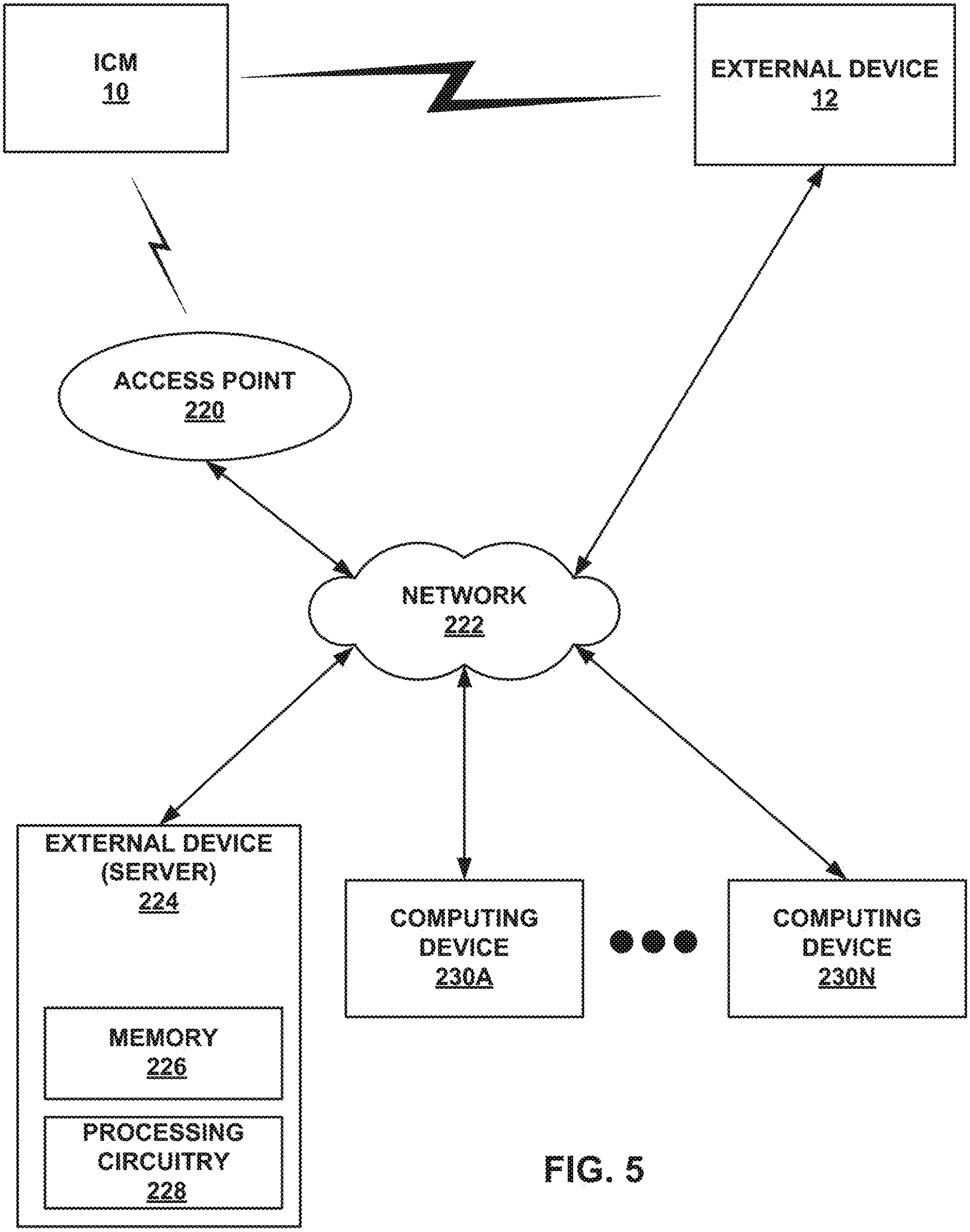
FIG. 5 is a functional block diagram illustrating an example system that includes external computing devices.

FIG. 5 is a functional block diagram illustrating an example system (e.g., system 8) that includes external computing devices. The system may include a ICM 10 and other devices (e.g., devices 12 or 62). For example, such devices may include external device 12, server 224 and one or more other computing devices 230A-230N, that are coupled to ICM 10 via a network 222. In this example, ICM 10 may use its communication circuitry 50 to communicate with external device 12 via a first wireless connection, and to communicate with an access point 220 via a second wireless connection. In the example of FIG. 5, access point 220, external device 12, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with the patient. Access point 220 may interrogate ICM 10 (e.g., periodically or in response to a command from the patient or network 222), to retrieve fluorescent marker measurements, cardiovascular pressure measurements, times of day, corresponding patient physiological phenomena data, or other operational or patient data from ICM 10. Access point 220 may provide the retrieved data to server 224 via network 222.

In some cases, server 224 may be configured to provide a secure storage site for data that has been collected from ICM 10 or external device 12. In some cases, server 224 may assemble data in web pages or other documents for viewing by trained professionals, such as clinicians, via computing devices 230A-230N.

In some examples, one or more of access point 220, server 224, or computing devices 230 may be configured to perform (e.g., may include processing circuitry configured to perform), some or all of the techniques described herein (e.g., with respect to processing circuitry 44 of ICM 10). In the example of FIG. 5, server 224 includes a memory 226 to store fluorescent marker information, heart rate, activity level, and respiration rate, received from IMD 10 or external device 12, and processing circuitry 228, which may be configured to provide some or all of the functionality ascribed to processing circuitry 44 of ICM 10.

Figure 6:
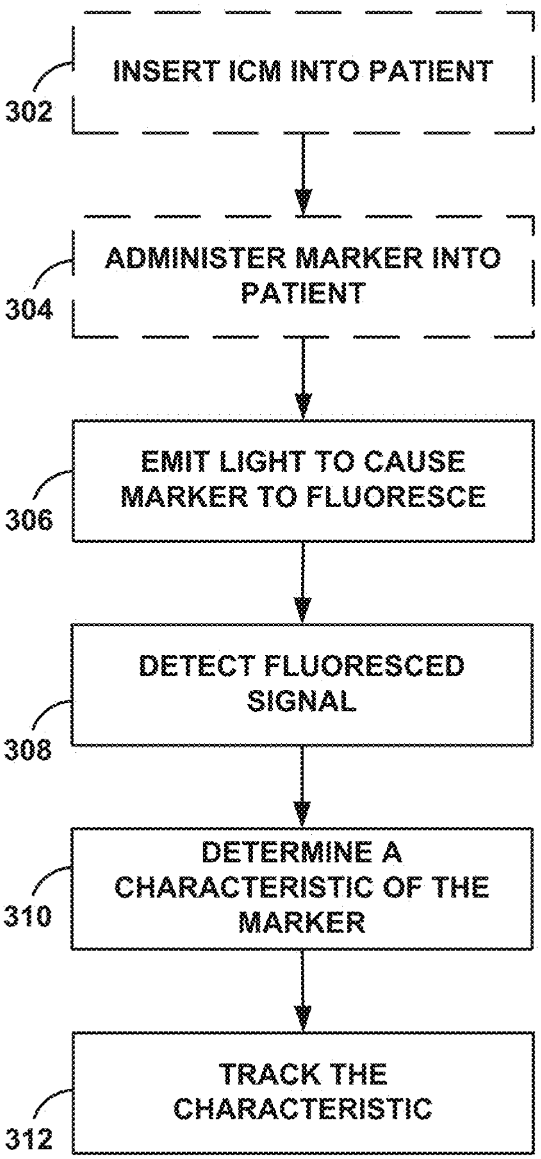
FIG. 6 is a flowchart illustrating an example technique that may be implemented using an implantable medical device.
Figure 7:
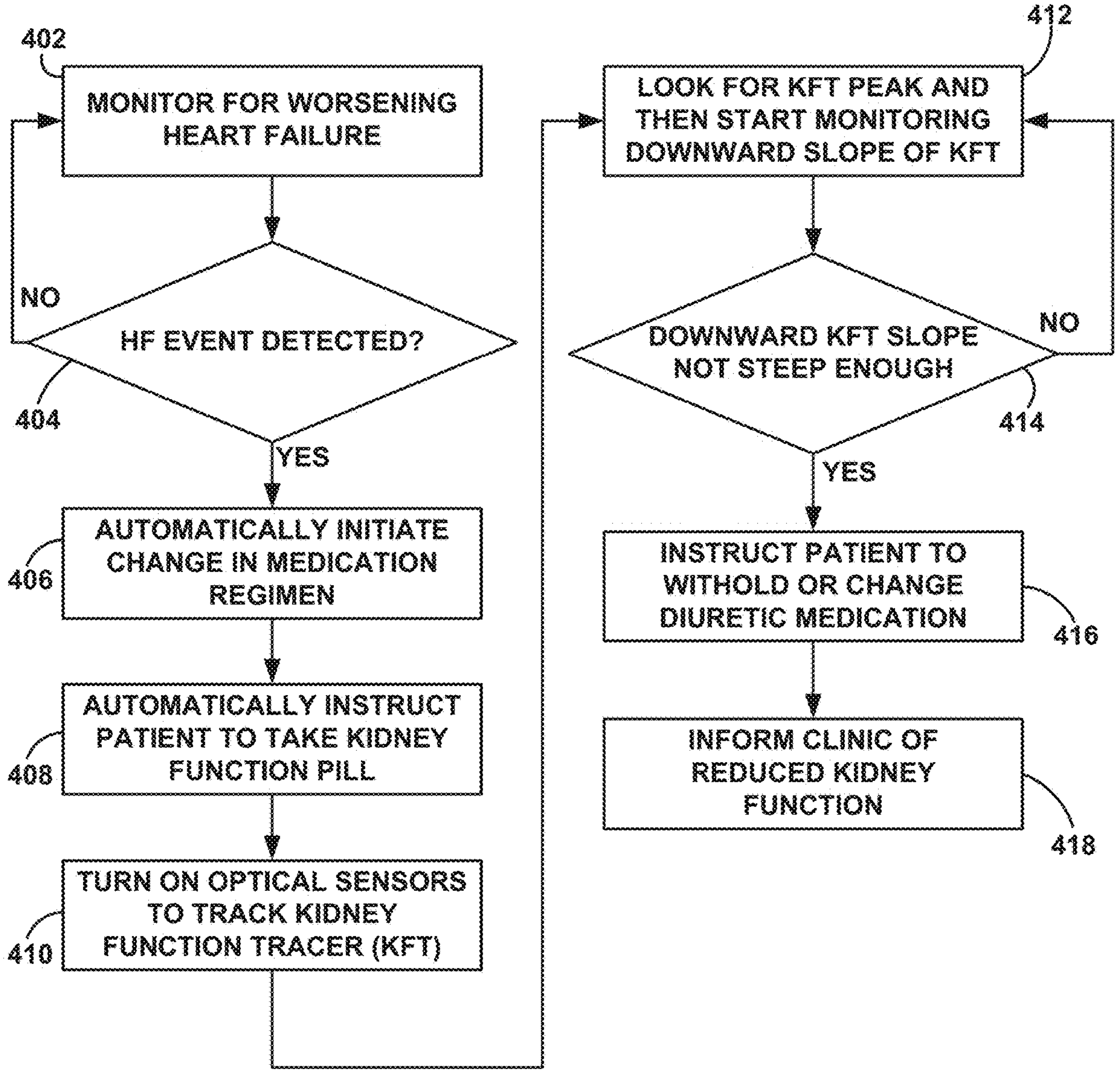
FIG. 7 is a flowchart illustrating an example technique that may be implemented using an implantable medical device to monitor heart and kidney function.
Figure 8:
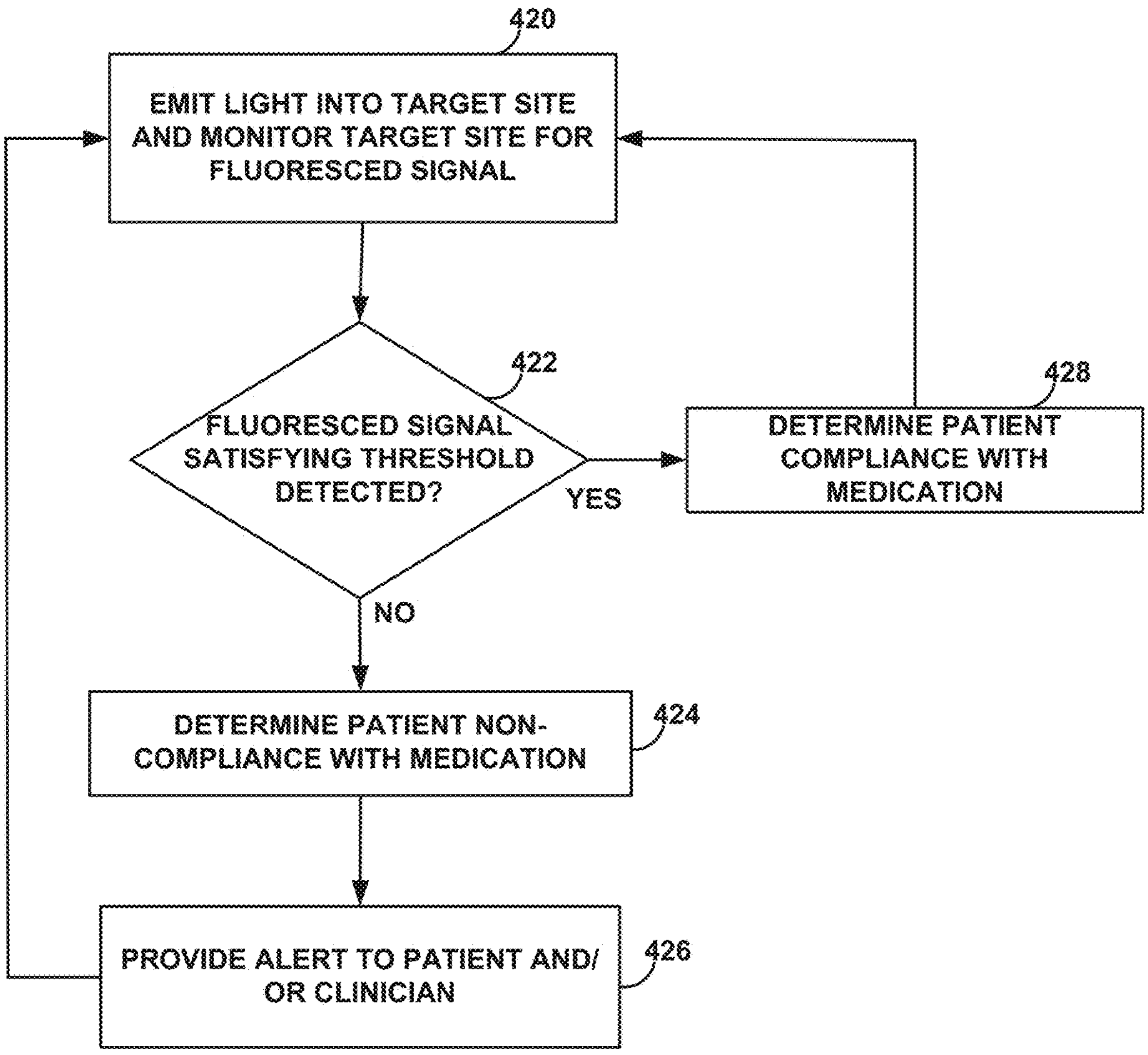
FIG. 8 is a flowchart illustrating an example technique that may be implemented using an implantable medical device to monitor patient compliance with a medication regimen.
Figure 9:
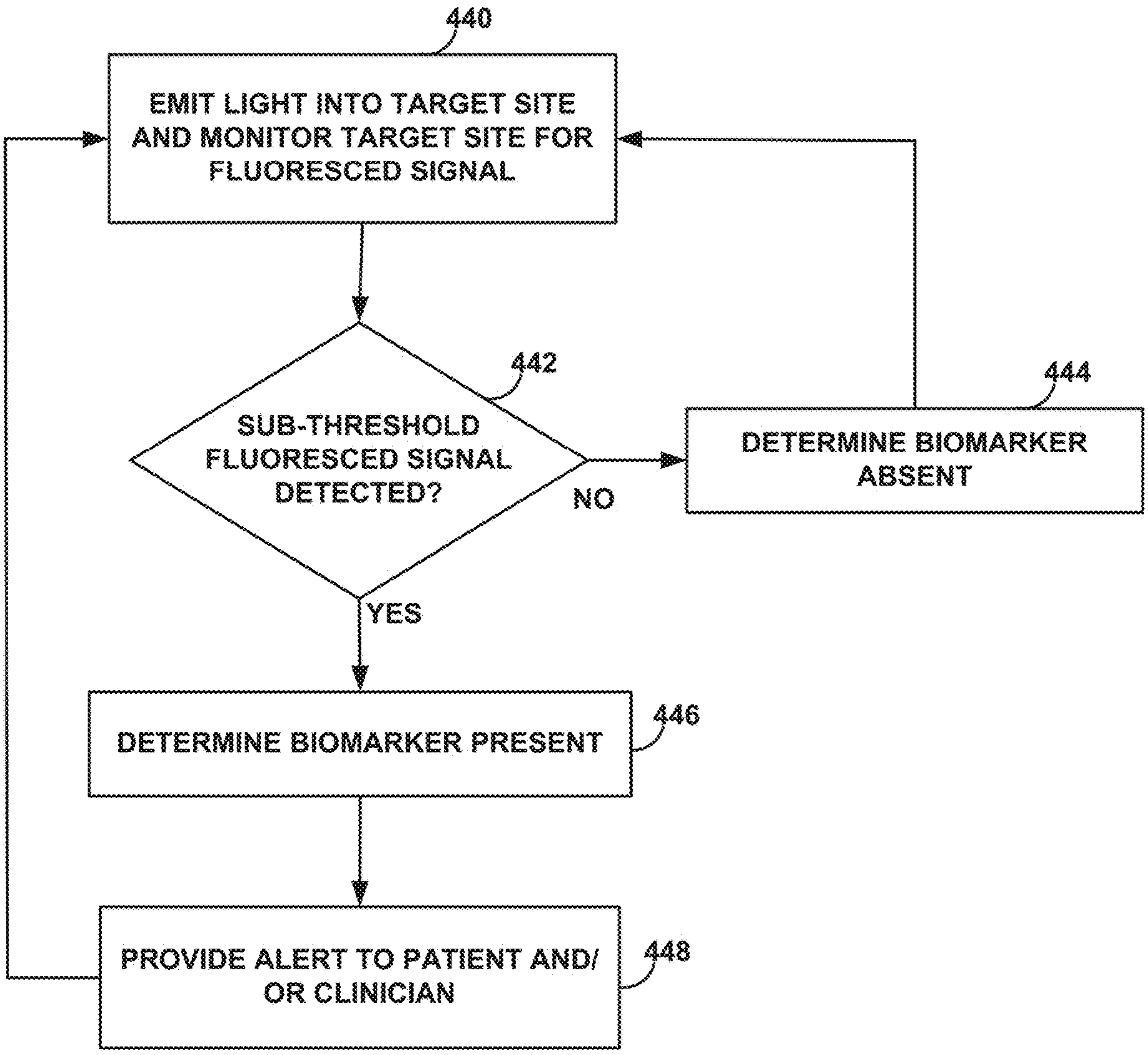
FIG. 9 is a flowchart illustrating an example technique that may be implemented using an implantable medical device to monitor the presence or absence of a biomarker within a patient.

FIGS. 6-9 are flowcharts illustrating example techniques for monitoring a marker (e.g., a fluorescent marker) within a patient that may be implemented by the systems and medical devices described herein, in the context of determining organ function, patient compliance with medication, and/or biomarker detection. FIG. 6 is a flowchart illustrating a general example technique for monitoring a marker within the patient. FIG. 7 is a flowchart illustrating an example technique for monitoring a marker in the context of determining organ function of the patient, such as heart and kidney function in the context of a patient with diagnosed or suspected heart failure. FIG. 8 is a flowchart illustrating an example technique for monitoring a marker in the context of determining patient compliance with a medication regimen. FIG. 9 is a flowchart illustrating an example technique for monitoring a marker in the context of detecting a biomarker within the patient. Although the example techniques illustrated in the flowcharts of FIGS. 6-9 as being implemented using ICM 10, any such example techniques may be implemented using other example medical devices, such as a medical device that is partially or completely external to the patient (e.g., a medical device that includes an externally-positioned patch).

FIG. 6 is a flowchart illustrating an example technique that may be implemented using an IMD system. ICM 10 may be inserted into patient 2, such as may be performed by a physician (302). A marker may be administered to patient 2 (304). In an example, a health care provider such as the physician administers the marker (e.g., a fluorescent marker) to patient 2. In some examples, patient 2 self-administers the marker. In some examples, a device may be configured to administer the marker, such as a drug pump or an automated intravenous drug delivery system. The dashed outline for boxes 302 and 304 may represent that a user (e.g., physician or the patient) or device (e.g. a drug pump) other than ICM 10 performs that step. In some examples, markers and drugs may be administered to patient 2 via ingestion. In some examples, ICM 10, an external device 12, access point 220, or computing device 230 provides an indication for patient 2 to take a drug or a marker, or for a caregiver to administer the drug or marker. In some examples, markers and drugs may also be administered intravenously.

Light emitter 38 may emit light, such as light having particular parameters as described below, that causes the marker to fluoresce (306). Light detector 40 may detect a fluoresced signal (308). Processing circuitry 44 (and/or processing circuitry 228 of server 224, processing circuitry 43 of external device 12 or processing circuitry 45 of implanted device 62) may determine one or more characteristics of the marker (310). For example, if the characteristic of the marker is a metabolism profile, and if the marker's metabolism profile is indicative of a drug metabolism profile, then information about the patient's metabolism of the drug may be determined by ICM 10. ICM 10 may track the characteristic over time (312). In some examples, ICM 10 instructs another device, or the clinician to initiate or change a therapy based on the tracked characteristic.

FIG. 7 is a flowchart illustrating an example technique that may be implemented by an IMD (e.g., ICM 10), alone or in combination with an external device, (e.g., external device 12) or other networked device that include processing circuitry, in accordance with this disclosure. As described herein, ICM 10 may monitor cardiac activity, among other things. Using electrodes 16, ICM 10 may monitor the patient for heart failure, or worsening of heart failure (402). If a heart failure (HF) event is detected (404), then ICM 10 may automatically initiate a change in the patient's medication regimen (406), e.g., via communication with the patient or a clinician via external device 12. For example, if the patient's medication regimen of a diuretic is changed based on detection of an HF event by ICM 10, external device 12 may instruct the patient to begin taking the diuretic, stop taking the diuretic, or increase or decrease a dosage of the diuretic. In some examples, a clinician may approve medication instructions.

In this example, ICM 10 may automatically instruct the patient to take a kidney function pill (408). In some examples, ICM 10 may transmit patient signals to external device 12, where external device 12 may be configured to process the signal information and interface with a user (e.g., thereby allowing for a clearance profile to not be required to be stored in ICM 10). In an example, the kidney function pill may comprise a fluorescent marker, where its kidney clearance profile is stored in the memory of ICM 10 or may be measure by ICM 10. ICM 10 may turn on its optical sensors (e.g., light emitter 38 and light detector 40) to track the kidney function tracer (KFT) (410). In an example, ICM 10 may monitor a characteristic of the KFT, such as a peak amount or amount over time. For example, ICM 10 may look for and determine a peak and then start monitoring the downward slope of the KFT over time (412). If the downward slope is not steep enough (414), then for example, ICM 10 may instruct the patient to withhold or change the diuretic medication regimen (416). Throughout the process, ICM 10 may inform the clinic or a clinician of the state of the patient or the state of the fluorescent marker. In an example, ICM 10 may inform the clinician of reduced kidney function (418), so that the clinician may provide appropriate health care. In this way, by tracking the fluorescent marker and monitoring the cardiac activity of the heart, clinicians may be provided with a better, more complete view of the patient's health, and better clinical outcomes may be achieved.

FIG. 8 is a flowchart illustrating an example technique that may be implemented by an IMD (e.g., ICM 10), alone or in combination with an external device, (e.g., external device 12) or other networked device including processing circuitry configured to monitor patient compliance with a medication regimen. According to the example of FIG. 8, processing circuitry (e.g., processing circuitry 44 of ICM 10) may control light emitter 38 to emit light into a target site within patient 2, and receive a signal corresponding to light detected by light detector 40 (e.g., a fluoresced signal) at the target site (420). In some examples, one or more parameters of the fluoresced signal, such as an amplitude of the signal, may be indicative of a level (e.g., a concentration) of a medication within the target site. Processing circuitry 44 then may determine whether a parameter of a detected fluoresced signal satisfies a threshold, such as a threshold amplitude value (422). If the parameter of the detected fluoresced signal does not satisfy the threshold (e.g., processing circuitry 44 does not detect a fluoresced signal or detects a fluoresced signal that does not satisfy the threshold) ("NO" at 422), then processing circuitry 44 determines that patient 2 is not compliant with a medication regimen (424).

After determining that patient 2 is not compliant with the medication regimen, processing circuitry 44 may transmit the determination to an external device (e.g., external device 12 or another external device). Processing circuitry 43 of external device 12 may cause user interface 66 to display a visual alert indicating that patient 2 is not compliant with the medical regimen, which may be viewed by a user of external device 12, such as patient 2, a clinician, or another user (426). In other examples, processing circuitry 43 may cause user interface 66 to generate an audible or other alert, such as via a speaker. If the parameter of the detected fluoresced signal satisfies the threshold ("YES" at 422), then processing circuitry 44 determines that patient 2 is compliant with the medication regimen (428). In some examples, processing circuitry 43 of external device 12 optionally may cause user interface 66 to generate a visible or audible alert indicating that patient 2 is compliant with the medication regimen, such as to provide encouragement to patient 2 to maintain compliance with the medication regimen and/or provide the clinician or other user with confirmation of patient 2's compliance. In this manner, tracking a fluorescent marker associated with a medication (e.g., coupled with molecules of the medication or otherwise delivered to patient 2 with the medication) may help enable patient 2 and/or the clinician to improve and/or maintain patient 2's compliance with his or her medication regimen(s). Improved and/or maintained compliance with one or more medication regimen(s) may help patient 2 achieve and/or maintain a desirable clinical outcome.

FIG. 9 is a flowchart illustrating an example technique that may be implemented by an IMD (e.g., ICM 10), alone or in combination with an external device, (e.g., external device 12) or other networked device that include processing circuitry, in accordance with this disclosure, to monitor the presence or absence of a biomarker within a patient. According to the example of FIG. 9, processing circuitry (e.g., processing circuitry 44 of ICM 10) may control light emitter 38 to emit light into a target site of patient 2, and receive a signal corresponding to light detected by light detector 40 (e.g., a fluoresced signal) at the target site (440). In some examples, one or more parameters of the fluoresced signal, such as an amplitude and/or emission frequency of the signal, may be indicative of a presence or level of a biomarker within the target site. As discussed above, a biomarker of interest may be associated with one or more of an organ function or a health condition (current or past) of patient 2. For example, the biomarker may be associated with kidney function, heart function, heart attack, stroke, cancer, or other organ functions or health conditions. Processing circuitry 44 then may determine whether a sub-threshold fluoresced signal is detected (442). A sub-threshold fluoresced signal may be indicative of the presence of the biomarker or of a particular amount or concentration of the biomarker within the target site, as discussed above. For example, patient 2 or a clinician may administer a fluorescent biomarker to patient 2, such as orally. If a parameter (e.g., amplitude) of the detected fluoresced signal satisfies or exceeds a threshold value (e.g., processing circuitry 44 determines that the parameter of the fluoresced is not sub-threshold) ("NO" at 442), then processing circuitry 44 determines that the biomarker is absent (444).

If processing circuitry 44 instead determines that the parameter of the fluoresced signal is sub-threshold ("YES" at 442), then processing circuitry 44 determines that the biomarker is present (446). After determining that the biomarker is present, processing circuitry 44 may transmit the determination to an external device (e.g., external device 12 or another external device). Processing circuitry 43 of external device 12 may cause user interface 66 to display a visual alert indicating that the biomarker is present, which may be viewed by a user of external device 12, such as patient 2, a clinician, or another user (448). In other examples, processing circuitry 43 may cause user interface 66 to generate an audible or other alert, such as via a speaker. In some examples, processing circuitry 43 of external device 12 optionally may cause user interface 66 to generate a visible or audible alert indicating that the biomarker is not present after determining that the biomarker is absent at 444. Such information pertaining to patient 2's health condition may help enable the clinician to determine an appropriate treatment for the health condition if such treatment is appropriate, which may help patient 2 achieve and/or maintain a desirable clinical outcome.

In some examples, techniques for monitoring a fluorescent marker within patient 2 may include monitoring one or more other patient parameters, such as one or more physiological parameters. In an example, using accelerometer 60, ICM 10 may monitor patient activity. Patient activity may include, among other things, physical activity (e.g., gross body movement), posture, or cardiac activity. Processing circuitry 44 (or other processing circuitry of a medical device system) may track an activity signal sensed using accelerometer 60. By sensing the activity signal, activity trends and compliance trends may be monitored, such as may help with diagnosing and guiding compliance issues. For example, if a patient has better compliance when they are not feeling well (such as may be characterized by inactivity), then this may provide the physician insight into how to better treat the patient. For example, the physician may encourage the patient to comply to prevent the patient from not feeling well in the first place. In some examples, ICM 10 may provide an indication to the patient, e.g., via external device 12, or the external device may provide the indication.

In an example, ICM 10 may comprise electrodes 16 and/or sensors 58 configured to measure impedance and/or oxygen saturations within the device, and other measures such as blood pressure outside the device. The processing circuitry described herein may use these or other measures to determine patient compliance, organ function, a presence and/or amount of a biomarker, and/or other physiological phenomena that may be of interest.

In an example, the systems and techniques described herein include integrated diagnostics (e.g., using multiple measures, such as to provide a patient compliance indication). For example, measures including, but not limited to, heart rate and heart rate variability, may be used. For example, impedance, oxygen metrics (e.g., oxygen saturation), pulse transit time, or other measures may be used.

In an example, the fluorescent marker may be selected based on one or more factors, such as characteristics of the marker. In some examples, the marker be a betalain-class dye that has been rendered fluorescent as described above. In an example, the bioavailability of the fluorescent marker may be considered. In general, the bioavailability of the marker may need to be relatively high for the light detector to detect relatively small levels of the marker. The fluorescent marker may be delivered as a vehicle, in addition or as an alternative to as a coating. The marker vehicle may comprise a hydrophobic formulation with a relatively small molecular size and weight. In an example, the marker may be a charged molecule of a size that may freely pass through membranes of the gastrointestinal tract, while uncharged polar compounds may need to be bound to an acetyloxymethyl ester derivative that may make it membrane permeable. However, the functionality of the marker compound may be unmasked when non-selective esterases, such as may be commonly found in tissue, cleave the ester derivative. In an example, absorption and consequent diffusion of the marker compound may then be driven by biophysical and biochemical processes which may inform the localization and specification of the optical system (e.g., the light emitter, light detector, and processing circuitry).

In an example, the pharmacokinetics of the fluorescent marker may be considered. The pharmacokinetics of the marker compound may be matched (e.g., correspond as described herein) to the drug kinetics. This behavior may be used to track dosing of a drug because the behavior of the marker may match the wash-in and wash-out behavior of the drug itself. In an example, the pharmacokinetics of the marker compound may be different than the drug kinetics. In this example, this behavior may be used to track and log the administration of the drug but may not be able to be used to track dosing.

In an example, the nature of the fluorescence of the fluorescent marker may be considered. The fluorescence characteristics of the marker compound may vary, such as depending on which marker is used. For example, depending on the fluorescence characteristics, different optical systems may be required. For example, different markers may exhibit different spectral properties, and thus may require different optical systems for detection. In an example, the marker compound may be autofluorescent, and as such, the optical requirements may include an emission capture optical sensor without needing a light source to excite the marker compound. In other examples, the marker compound may be photo-reactive, and as such, the optical requirements may include one or more optical light sources (e.g., light emitters such as diodes) with specific wavelength(s) tuned to the photo-reactive compound and one or more optical detectors to capture the resulting emission upon excitation.

In an example, the marker compound may be a non-fluorescent compound that chelates or binds to native proteins and shifts their native photo-reactivity of the protein (e.g., Stokes spectral shift or a stereochemical configuration shift and chirality change such as indole derivatives with nitroalkenes). Thus, the compound may have a high $K_d$ (dissociation constant) with a low affinity for binding, so as not to compete with biochemical processes. Many buffering compounds exist, and may be used with the present techniques. The chelating compound may then suppress the emission of a known plasma, interstitial or cellular protein, such as nicotinamide adenine dinucleotide (NADH), tryptophan or flavonoid based proteins (FAD).

In an example, the localization of the fluorescent marker may be considered.

The nature of fluorescence, bioavailability, pharmacokinetics, and its location in the body will drive the implant location or the placement of the external patch.

The localization of the optical system would need to match the localization of the marker, since compounds that are systemic would need optical systems implanted or positioned externally close to a major blood vessel. However, compounds that localize interstitially would not need this consideration. However, compounds that localize or concentrate lymphatically, in the central nervous system, crossing the blood brain barrier and/or urinary track, would require optical sensor localization close to these regions.

In some examples, the information resulting from detecting the fluorescence of the marker, whether based on excitation or auto-fluorescence, may be processed using standard techniques (e.g., signal processing techniques including filtering and amplifying signals). In an example, ICM 10 may use one excitation source (e.g., a first emitter) to activate the marker compound. In an example, ICM 10 may use multiple excitation sources (e.g., multiple light emitters) to activate one or more marker compounds or take out background noise. In some examples, the systems and techniques, as described herein., may include a spectral light sweep, a monochromatic light (e.g., a single wavelength range), or a multi-wavelength light (e.g., white light). In some examples, the ICM 10 may not be required to use the (or may not need to include) the light emitter, such as if the marker being used is natively or artificially fluorescent. The medical system detection of the fluoresced signals may be filtered around a specific wavelength bandwidth, or may include a range of wavelengths.

In an example, the emission system may utilize a single emission sensor (e.g., including the light emitter) tuned to a specific wavelength, a single emission sensor that alternates spectral sensitivity, or multiple simultaneously active sensors to capture fluorescence at multiple wavelength simultaneously. The processing of the collected light signal may be on a single emission source or may utilize radiometric techniques for artifact, background, and dosage subtraction. The detection of the light signal may then result in a signal that can be processed using standard techniques, such as a change in intensity (e.g., using an amplitude change for the same wavelength for the spectral peak), a change in spectral response (e.g., using a shift of the spectral peak with the same amplitude), a change in background noise (e.g., using a DC offset change or baseline drift), or a subtraction or elimination of a native background signal at a specific wavelength.

In some examples, the optical system may be distributed with different components of the system communicating with one another to complete the excitation, emission, and processing tasks. In some examples, the techniques described herein may be performed in real time, or may be processes offline, such as at a monitoring center.

All of the examples described herein with respect to a compound may also apply with respect to a single molecule or a uniform substance.

In some examples, different types of implantable medical devices may be configured to perform the techniques described herein, and as such, may be configured to include a light emitter and a light detector. Examples of such device may include, a subcutaneous device, a pacemaker, defibrillator, a pressure sensor, a drug pump, a neurostimulator, or another medical device.

Experimental Results

The following is a description of experimental results that have been obtained from a study pertaining to the subject matter of this disclosure. The experimental results described herein are illustrative in nature and are not intended to limit the example devices, systems, and techniques described above.

Study Protocol: The purpose of the study was to investigate in an acute or semi-chronic rat trial set-up if fluorophores are detectable in the ISF (InterStitial Fluid) when injected IV or given to the rat Per Oral (PO). Four rat subjects (Rat 001, Rat 002, Rat 003, and Rat 004) were included in the study. The procedure of the study was as follows: Rat subjects were Sprague Dawley rats, male, Diet Induced Obese (DIO). For each rat, the rat was anaesthesized, shaved and cleaned on the back for PMMA optical fiber insertion. A tail venous catheter was placed and two 250 um optical PMMA fibers were placed in the subcutaneous fat tissue of the DIO rat. The base and tape of the sensor unit was sutured to the skin.

For Rats 001 and 002, a reader device suitable for indocyanine green dye detection was mounted. [ . . . ]Rat 002 died during oral dosing while under anesthesia due to lack of swallowing reflex.

For Rats 003 and 004 reader devices suitable for Alexa Fluor 594™ (AF594) detection were mounted. Recording began using RF data transfer (GST protocol, MDT Diabetes). A first IV injection of 0.01 mg AF594 was injected (1 mL into tail vein). Rise and decay of fluorescence was observed before a second injection of 1 mL of 0.01 mg AF594 into the tail vein. Anesthesia then was removed and the rat was placed into a cage. The following day, the rat was orally dosed with 0.1 mg AF594 (1 mL) in the morning and orally dosed with 0.5 mg AF594 (1 mL) in the afternoon. Rat 003 and Rat 004 were successfully orally dosed in this manner, and then were placed into clean cages for urine collection.

Figure 10:
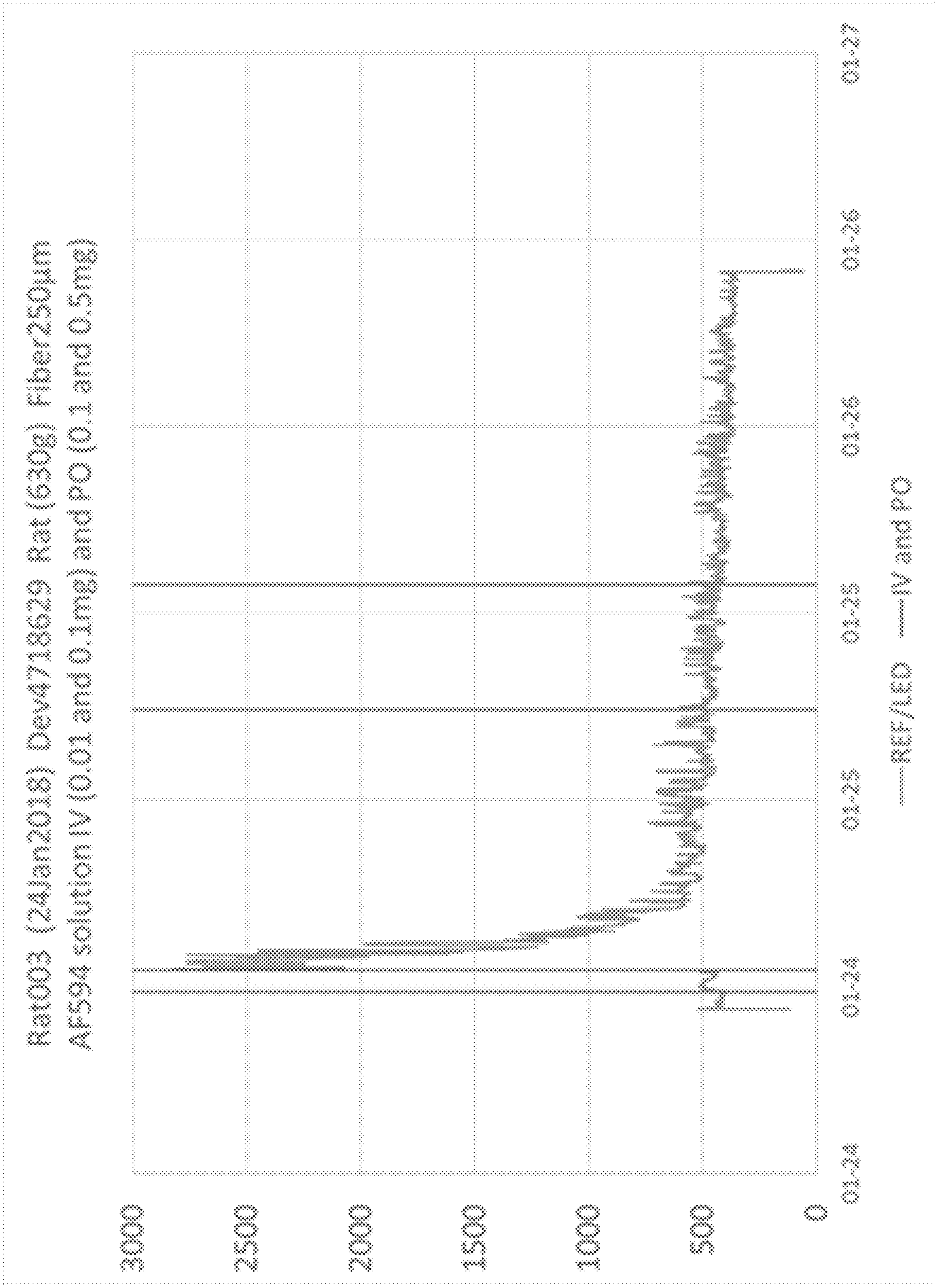
FIGS. 10-12B are graphical representations of experimental results obtained from a study pertaining to the subject matter of this disclosure.

Data obtained for Rat 003 is shown in FIG. 10. The two left-most vertical lines in FIG. 10 represent IV injections of AF594 on Jan. 24, 2018. The two right-most vertical lines in FIG. 10 represent the PO dosages of AF594 on Jan. 25, 2018. The variable line extending along the x-axis represents observed fluorescence. Rat 003 was 630 g (approx. half is available water phase for distribution of dye). 0.01 mg AF594 per 630 g≈1.2 mg per 75 kg. 0.1 mg≈12 mg/75 kg body weight. 0.75 mg≈89 mg/75 kg body weight. (Used dye is approx. 500 USD/mg). "A" in FIG. 10 shows that the IV injection raised the signal with a non-noisy curve. The dye was cleared relatively fast from Rat 003. "B" in FIG. 10 shows that the second IV injection raised the signal significantly and Rat 003 woke making the data noise more apparent. Clearing of the dye had an approximate time-constant (t) of 2 hours (6 hours before "total" clearance). "C" in FIG. 10 shows no sign of PO dosing in Rat 003 ISF. The second device failed with Rat 003 due to poor alignment between the PMMA fiber and the device.

Figure 11:
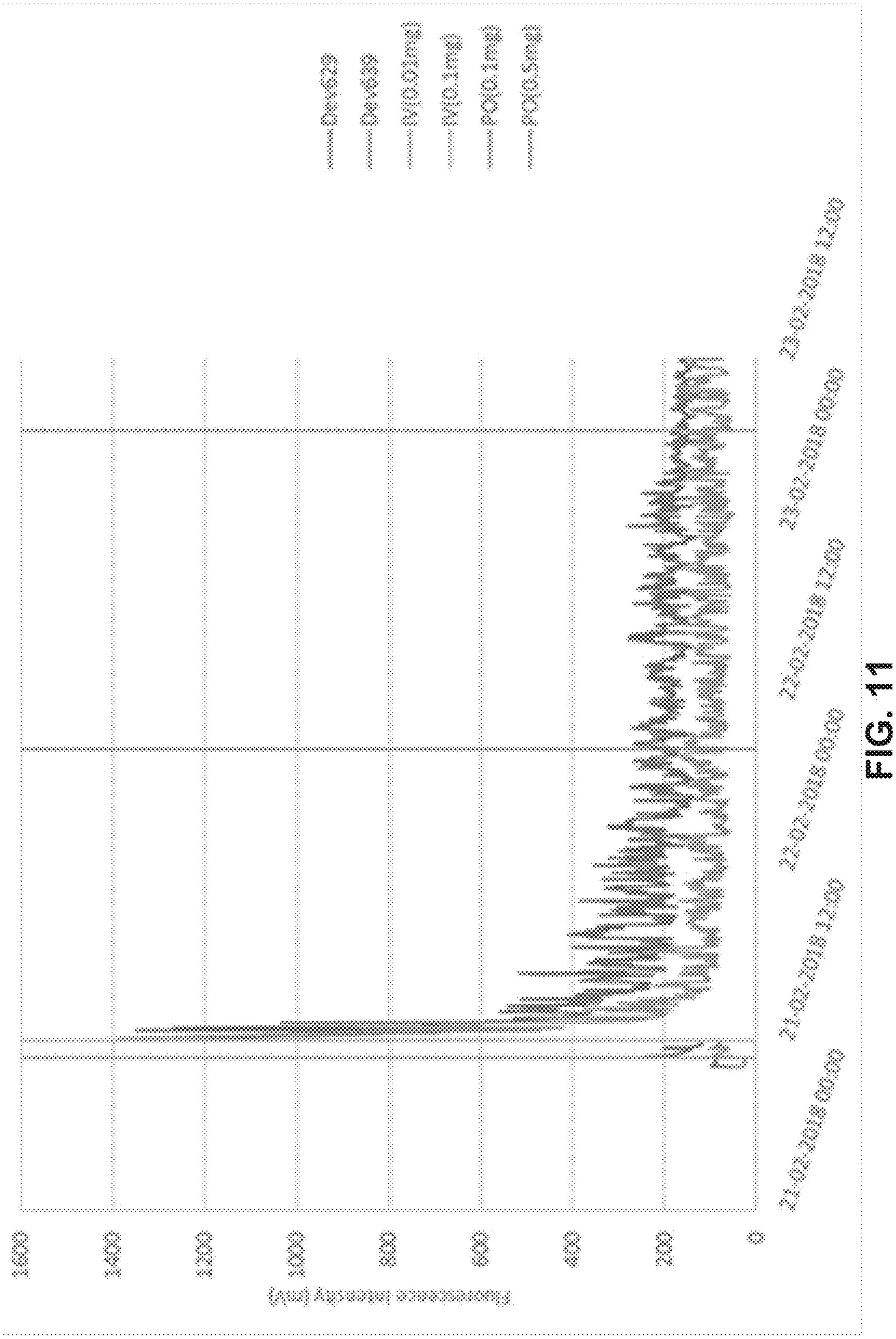

Data obtained for Rat 004 is shown in FIG. 11. The left-most vertical line in FIG. 11 represents an IV injection of 0.01 mg AF594 on Feb. 22, 2018. The second left-most vertical line in FIG. 11 represents an IV injection of 0.1 mg AF594 on Feb. 22, 2018. The second right-most vertical line in FIG. 11 represents a PO dosage of 0.1 mg AF594 on Feb. 22, 2018. The right-most vertical line in FIG. 11 represents a PO dosage of 0.5 mg AF594 on Feb. 23, 2018. The lower variable line extending along the x-axis represents observed fluorescence intensity for Device 629. The upper variable line extending along the x-axis represents observed fluorescence intensity for Device 639. Rat 004 was 660 g (approx. half is available water phase for distribution of dye). 0.01 mg AF594 per 660 g≈2.3 mg per 75 kg. 0.1 mg≈23 mg/75 kg. 0.5 mg≈92 mg/75 kg. "A" in FIG. 11 shows that the first IV injection raised the signal. The dye was cleared relatively fast from Rat 004. "B" in FIG. 11 shows that the second IV injection raised the signal significantly and the rat woke making the data noise more apparent. Clearing of the dye had an approximate time-constant (t) of 2 hours (6 hours before "total" clearance). "C" in FIG. 11 shows no sign of PO dosing in Rat 004 ISF. However, the spectrum of urine showed clear signs of AF594.

Figure 12A:
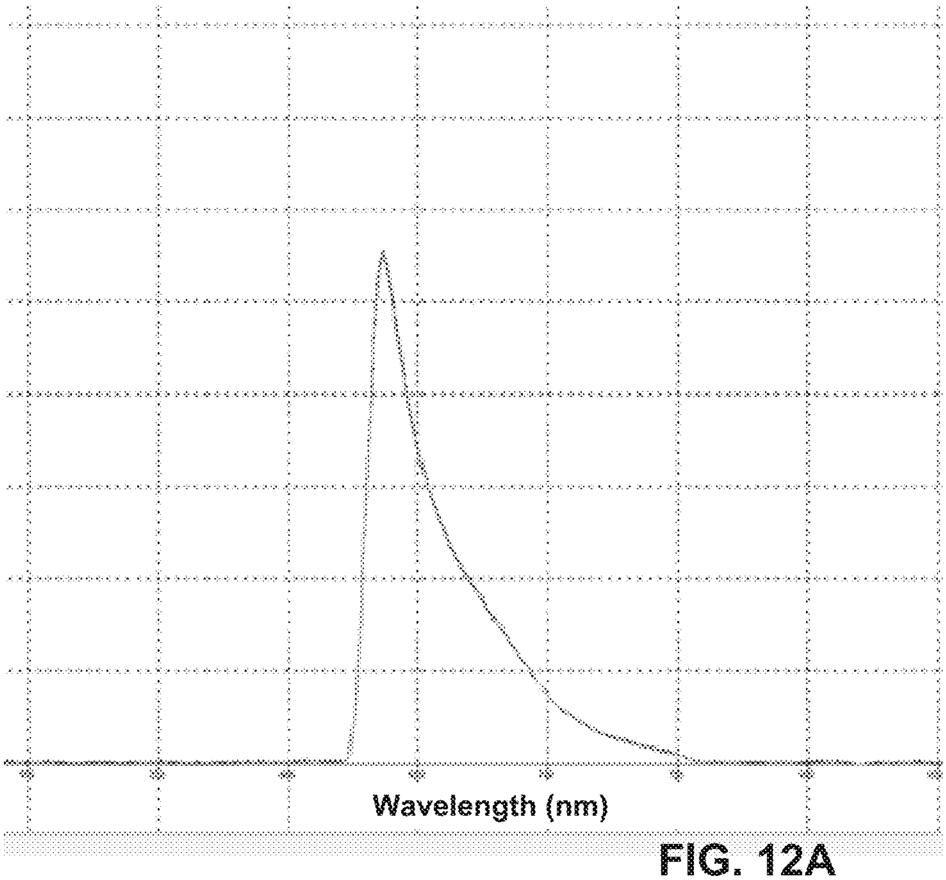
Figure 12B:
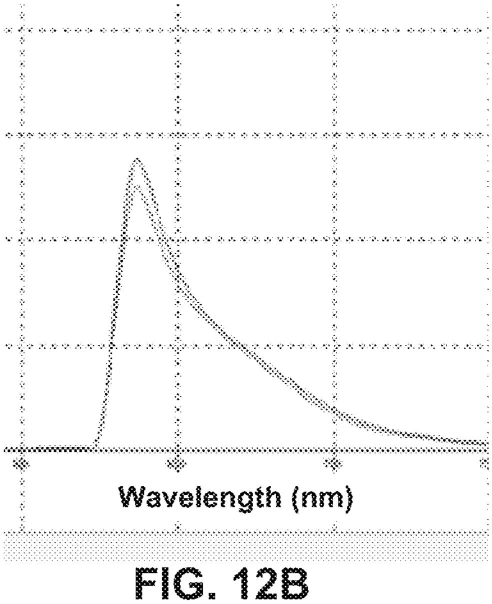

Raw urine spectrum of Rat 004, including AF594, is shown in FIG. 12A. An inset of Rat 004 urine spectrum chart of FIG. 12A is shown in FIG. 12B, with total signal from urine separated from signal from AF594. The line having the higher peak represents the full urine signal and the line having the lower peak represents the signal from the AF594 concentration in the urine, which was 3.2 μg/mL.

Rat 001 dosing Indo Cyanine Green IV showed distinct signals and relatively fast clearance from the ISF. Rat 002 with attempted PO dosing while the rat was anesthetized was non-successful; Rat 002 died (drowning due to lack of swallowing reflex during anesthesia). Rat 003 and Rat 004: Dosing AF594 IV and PO (PO while the rat was awake) yielded useful information. IV injections can be followed in ISF using an optical reader device and a Ø250 μm optical PMMA fiber. There is significant noise in the system when the rat is awake. PO dosing cannot be observed in the ISF even after dosing large amounts of dye. 800 μL urine collected 6 hours after high PO dosing show "traces" of AF594 (Ocean Optics spectrum).

Based on the experiments, the inventors determined that IV dosing when anesthetized or awake (IV catheter cannot sit in the tail when awake) provided adequate ability to detect the marker in ISF. PO dosing using the tested markers was challenging to detect in ISF. This could be due to the dye passing from the gastrointestinal tract to the blood slower than the kidneys are capable of clearing the dye from the body. Other dyes as described herein, e.g., with different gastrointestinal absorption and metabolism profiles, may be adequately present in ISF for detection.

The following numbered clauses demonstrate one or more aspects of the disclosure.

Clause 1: In one example, a medical system comprises: a medical device comprising: a housing configured to be implanted in a target site of a patient; a light emitter on or within the housing, the light emitter configured to emit a signal into the target site, wherein the emitted signal is configured to cause a fluorescent marker to emit a fluoresced signal; and a light detector on or within the housing, the light detector configured to detect the fluoresced signal; and processing circuitry at least partially within the housing and coupled to the light emitter and the light detector, the processing circuitry configured to determine a characteristic of the fluorescent marker based on the emitted signal and the fluoresced signal, wherein the characteristic of the fluorescent marker is indicative of a presence of a compound in the patient, wherein the processing circuitry is configured to track the presence of the compound of the patient based on the characteristic of the fluorescent marker.

Clause 2: In some examples of the medical system of clause 1, the fluorescent marker is administered into the patient, and wherein the emitted signal is configured to cause the fluorescent marker administered into the patient to emit the fluoresced signal.

Clause 3: In some examples of the medical system of clause 1 or 2, the processing circuitry is configured to determine the patient's compliance in taking a medication based on the characteristic of the fluorescent marker, the system further comprising output circuitry coupled to the processing circuitry, the output circuitry configured to provide a patient compliance indication in response to the determination, wherein the patient compliance indication is indicative of the patient's compliance in taking the medication.

Clause 4: In some examples of the medical system of clause 3, the medical device further includes input circuitry coupled to the processing circuitry, the input circuitry configured to receive information about a medication for the patient, wherein the processing circuitry is configured to determine a medication level based on the information about the medication and the characteristic of the fluorescent marker and configured to determine the patient's compliance in taking the medication based on the medication level, and wherein the information about the medication includes at least one of an administration time, a dosage, a medication type, an anticipated medication metabolism profile, or a medication history.

Clause 5: In some examples of the medical system of clause 4, the presence of the compound is indicative of a physiological phenomenon that comprises a medication metabolism of the patient, and wherein the processing circuitry is configured to determine a measure of the actual medication metabolism based on the information about the medication and the characteristic of the fluorescent marker.

Clause 6: In some examples of the medical system of any of clauses 1-5, the signal configured to cause the fluorescent marker to emit the fluoresced signal comprises a first signal, the first signal comprising a first wavelength, wherein the light emitter is configured to emit a second signal into the target site of the patient, the second signal comprising a second wavelength, wherein the light detector is configured to detect the second signal, and wherein the processing circuitry is configured to determine background noise using the second signal, and determine the characteristic of the fluorescent marker based on the background noise.

Clause 7: In some examples of the medical system of any of clauses 1-6, the signal configured to cause the fluorescent marker to emit the fluoresced signal comprises a first signal, the first signal comprising a first wavelength, wherein the light emitter is configured to emit a second signal into the target site of the patient, the second signal comprising a second wavelength, and wherein the fluorescent marker comprises a first fluorescent marker, the fluoresced signal comprises a first fluoresced signal, and the presence of the compound is indicative of a first physiological phenomenon of the patient; and wherein the second signal is configured to cause a second fluorescent marker to emit a second fluoresced signal, wherein the light detector is configured to detect the second fluoresced signal, and wherein the processing circuitry is configured to determine a characteristic of the second fluorescent marker based on the second signal and the second fluoresced signal, the characteristic of the second fluorescent marker indicative of a second physiological phenomenon of the patient.

Clause 8: In some examples of the medical system of any of clauses 1-7, the presence of the compound is indicative of a first physiological phenomenon, wherein the medical system further comprises a sensor configured to sense a second physiological phenomenon of the patient, wherein the processing circuitry is configured to detect that the second physiological phenomenon meets a criterion, wherein the processing circuitry is configured to determine the patient's compliance in taking a medication based on the characteristic of the fluorescent marker, and wherein the medical system further comprises output circuitry coupled to the processing circuitry, the output circuitry is configured to provide a patient compliance indication upon determining that the second physiological phenomenon meets the criterion and determining the patient's compliance.

Clause 9: In some examples of the medical system of any of clauses 1-8, the housing is configured to be subcutaneously implanted in a patient, and the medical device comprises: at least one electrode on the housing; and sensing circuitry coupled to the at least one electrode and configured to sense a cardiac electrogram via the at least one electrode, and wherein the processing circuitry is configured to monitor cardiac activity of the patient based on the cardiac electrogram.

Clause 10: In some examples of the medical system of clause 9, the processing circuitry is configured to determine a heart failure event based on the monitored cardiac activity of the patient, wherein the medical system further comprises output circuitry coupled to the processing circuitry, the output circuitry configured to provide a patient medication instruction corresponding to the administration of a dose of the fluorescent marker, wherein the presence of the compound corresponds to kidney function of the patient, and wherein the processing circuitry is configured to track the characteristic of the fluorescent marker in response to the patient's compliance with the medication instruction.

Clause 11: In some examples of the medical system of any of clauses 1-10 the housing is configured to be subcutaneously implanted in a patient, and the medical device comprises: an accelerometer within the housing; sensing circuitry coupled to the accelerometer and configured to sense an activity signal via the accelerometer, and wherein the processing circuitry is configured to monitor activity of the patient based on the activity signal.

Clause 12: In some examples of the medical system of any of clauses 1-11, the target site including a site proximate to well vascularized tissue or a heart of the patient.

Clause 13: In some examples of the medical system of any of clauses 1-12, the presence of the compound is indicative of a physiological phenomenon that corresponds to one of an organ absorption or an organ clearance of the fluorescent marker, the characteristic of the fluorescent marker corresponding to one of a respective organ absorption profile or organ clearance profile of the fluorescent marker, and wherein the processing circuitry is configured to determine a peak of the tracked characteristic of the fluorescent marker.

Clause 14: In some examples of the medical system of clause 13, the fluorescent marker is configured to bind to at least one of a biomarker or an injected substrate.

Clause 15: In some examples of the medical system of any of clauses 1-14, the medical device is an implantable medical device (IMD).

Clause 16: In some examples of the medical system of any of clauses 1-15, the medical device comprises a patch.

Clause 17: In some examples of the medical system of any of clauses 1-16, the presence of the compound includes the presence of one or more of: prostate-specific antigen (PSA), creatinine, B-type natriuretic peptide (BNP), or troponin.

Clause 18: In some examples of the medical system of any of clauses 1-17, the medical system further comprises a substrate on the housing, wherein the substrate is configured to interact with the compound.

Clause 19: In some examples of a method for tracking a fluorescent marker, the method comprises: emitting, by a light emitter, a signal into a target site of a patient, wherein the signal is configured to cause a fluorescent marker to emit a fluoresced signal; detecting, by a light detector, the fluoresced signal; determining, by processing circuitry, a characteristic of the fluorescent marker based on the emitted signal and the fluoresced signal, wherein the characteristic of the fluorescent marker is indicative of a presence of the compound in the patient; and tracking, by the processing circuitry, the presence of the compound in the patient based on the characteristic of the fluorescent marker.

Clause 20: In some examples of the method of clause 19, the method further comprises determining, by the processing circuitry, the patient's compliance in taking a medication based on the characteristic of the fluorescent marker; and providing, by output circuitry, a patient compliance indication in response to the determination, wherein the patient compliance indication is indicative of the patient's compliance in taking the medication.

Clause 21: In some examples of the method of clause 20, the method further comprises receiving, by input circuitry, information about a medication for the patient; determining, by the processing circuitry a medication level based on the information about the medication and the characteristic of the fluorescent marker, and the patient's compliance in taking the medication based on the medical level; and wherein the information about the medication includes at least one of an administration time, a dosage, a medication type, an anticipated medication metabolism profile, or a medication history.

Clause 22: In some examples of the method of clause 21, the presence of the compound is indicative of a physiological phenomenon that comprises a medication metabolism of the patient, and the method further comprising determining, by the processing circuitry, a measure of the actual medication metabolism based on the information about the medication and the characteristic of the fluorescent marker.

Clause 23: In some examples of the method of any of clauses 19-22, the signal configured to cause the fluorescent marker to emit the fluoresced signal comprises a first signal, the first signal comprising a first wavelength; and the method further comprises: emitting, by the light emitter, a second signal into the target site of the patient, the second signal comprising a second wavelength; detecting, by the light detector, the second signal; and determining, by the processing circuitry, background noise using the second signal, wherein determining the characteristic of the fluorescent marker comprises determining the characteristic of the fluorescent marker based on the background noise.

Clause 24: In some examples of the method of any of clauses 19-23, the signal configured to cause the fluorescent marker to emit the fluoresced signal comprises a first signal, the first signal comprising a first wavelength, the method further comprising emitting, by the emitter, a second signal into the target site of the patient, the second signal comprising a second wavelength, wherein the fluorescent marker comprises a first fluorescent marker, the fluoresced signal comprises a first fluoresced signal, and presence of the compound is indicative of a first physiological phenomenon of the; and wherein the second signal is configured to cause a second fluorescent marker to emit a second fluoresced signal, the method further comprising: detecting, by the light detector, the second fluoresced signal; and determining, by the processing circuitry, a characteristic of the second fluorescent marker based on the second signal and the second fluoresced signal, the characteristic of the second fluorescent marker indicative of a second physiological phenomenon of the patient.

Clause 25: In some examples of the method of any of clauses 19-24, the presence of the compound is indicative of a first physiological phenomenon, the method further comprising: sensing, by a sensor, a second physiologic phenomenon of the patient; detecting, by the processing circuitry, that the second physiological phenomenon meets a criterion, determining, by the processing circuitry, the patient's compliance in taking a medication based on the characteristic of the fluorescent marker; and providing, by output circuitry, a patient compliance indication upon determining that the second physiological phenomenon meets the criterion and determining the patient's compliance.

Clause 26: In some examples of the method of any of clauses 19-25, the method further comprises sensing, by at least one electrode on a housing of a medical device, a cardiac electrogram, and monitoring, by the processing circuitry, cardiac activity of the patient based on the cardiac electrogram.

Clause 27: In some examples of the method of clause 26, the method further comprises determining, by the processing circuitry, a heart failure event based on the monitored cardiac activity of the patient; providing, by output circuitry, a patient medication instruction corresponding to the administration of a dose of the fluorescent marker, wherein the presence of the compound corresponds to kidney function of the patient; and tracking, by the processing circuitry, the characteristic of the fluorescent marker in response to the patient's compliance with the medication instruction.

Clause 28: In some examples of the method of clause 27, the target site includes a site proximate to a blood vessel or a heart of the patient.

Clause 29: In some examples of the method of any of clauses 19-28, the presence of the compound is indicative of a physiological phenomenon that corresponds to one of an organ absorption or an organ clearance of the fluorescent marker, the characteristic of the fluorescent marker corresponding to one of a respective organ absorption profile or organ clearance profile of the fluorescent marker, and the method further comprising determining, by the processing circuitry, a peak of the tracked characteristic of the fluorescent marker.

Clause 30: In some examples of the method of clause 29, the fluorescent marker is configured to bind to at least one of a biomarker or an injected substrate.

Clause 31: In some examples of the method of any of clauses 19-30, the fluorescent marker is administered into the patient, and wherein the emitted signal is configured to cause the fluorescent marker administered into the patient to emit the fluoresced signal.

Clause 32: In some examples, a medical system comprises a medical device comprising: a housing configured to be implanted in a target site of a patient; a light emitter on or within the housing, the light emitter configured to emit a signal into the target site to cause the emitted signal to reflect from a marker; and a light detector on or within the housing, the light detector configured to detect the reflected signal; and processing circuitry at least partially within the housing and coupled to the light emitter and the light detector, the processing circuitry configured to determine a characteristic of the marker based on the emitted signal and the reflected signal, wherein the characteristic of the marker is indicative of a presence of a compound in the patient, wherein the processing circuitry is configured to track the presence of the compound of the patient based on the characteristic of the marker.

Clause 33: In some examples of the medical system of clause 32, the emitted signal comprises a first wavelength, and wherein the reflected signal comprises a second wavelength.

Clause 34: In some examples of the medical system of clause 33, the first wavelength is different than the second wavelength.

Clause 35: In some examples of the medical system of clause 33 or 34, the second wavelength varies based on an amount of the marker present.

Clause 36: In some examples of the medical system of any of clauses 33-35, the second wavelength varies based on a condition of the marker.

Clause 37: In some examples, a non-transitory, computer-readable storage medium comprises instructions, that when executed, cause one or more processors to: emit, by a light emitter coupled to the one or more processors, a signal into a target site of the patient, wherein the signal is configured to cause a fluorescent marker administered into the patient to emit a fluoresced signal; detect, by a light detector coupled to the one or more processors, the fluoresced signal; and determine, by the one or more processors, a characteristic of the fluorescent marker based on the emitted signal and the fluoresced signal, wherein the characteristic of the fluorescent marker is indicative of a physiological phenomenon of the patient; and tracking, by the one or more processors, the physiological phenomenon of the patient based on the characteristic of the fluorescent marker.

Clause 38: In some examples, a system comprises means for emitting a signal into a target site of the patient, wherein the signal is configured to cause a fluorescent marker administered into the patient to emit a fluoresced signal; means for detecting the fluoresced signal; and means for determining a characteristic of the fluorescent marker based on the emitted signal and the fluoresced signal, wherein the characteristic of the fluorescent marker is indicative of a physiological phenomenon of the patient; and means for tracking the physiological phenomenon of the patient based on the characteristic of the fluorescent marker.

The examples described herein may be combined in any permutation or combination.

Various examples have been described. These and other examples are within the scope of the following claims.

What is claimed is:

1. A system comprising:

a medical device configured to be implanted within a patient, wherein the medical device is configured to collect an optical biometric signal over an extended period of time greater than seven days, wherein the optical biometric signal indicates a level of a substance associated with a medication within the patient;

a memory; and processing circuitry in communication with the memory, wherein the processing circuitry is configured to:

receive, from the medical device, the optical biometric signal;

identify, based on the optical biometric signal, a first level of the substance;

determine a trend of the level of the substance between a first time corresponding to the first level of the substance and a second time following the first time; and determine, based on the trend, whether to instruct the patient to alter the medication regimen or cease the medication regimen.

2. The system of claim 1, wherein the processing circuitry is further configured to instruct the patient to begin the medication regimen, and wherein to instruct the patient to begin the medication regimen, the processing circuitry is configured to instruct the patient to take a medication including the substance.

3. The system of claim 2, wherein to instruct the patient to begin the medication regimen, the processing circuitry is configured to output, to a user interface of a user device, an instruction for the patient to take a medication for regulating a kidney function of the patient.

4. The system of claim 1, wherein the system is configured to perform one of:

instruct, in response to determining to instruct the patient to alter the medication regimen or cease the medication regimen based on the trend, the patient to alter the medication regimen or cease the medication regimen; or instruct, in response to determining not to instruct the patient to alter the medication regimen or cease the medication regimen based on the trend, the patient not to alter the medication regimen or cease the medication regimen.

5. The system of claim 1, wherein the optical biometric signal comprises a fluoresced signal, wherein the processing circuitry is configured to output, to a user interface of a user device, an instruction for the patient to take a medication comprising a fluorescent marker, wherein to identify the first level of the substance, the processing circuitry is configured to determine a peak level of the fluorescent marker based on the fluoresced signal, and wherein to determine the trend of the level of the substance, the processing circuitry is configured to determine a trend of the level of the fluorescent marker between the first time and the second time.

6. The system of claim 1, wherein to determine the trend of the level of the substance, the processing circuitry is configured to:

determine the level of the substance over a period of time between the first time and the second time; and determine a slope of the level of the substance over the period of time between the first time and the second time, wherein to determine whether to instruct the patient to alter the medication regimen or cease the medication regimen based on the trend, the processing circuitry is configured to determine whether the slope of the level of the substance over the period of time between the first time and the second time is below a threshold slope value for more than a threshold amount of time.

7. The system of claim 6, wherein the processing circuitry is configured to:

determine to instruct the patient to alter the medication regimen or cease the medication regimen based on the slope of the level of the substance over the period of time between the first time and the second time being below the threshold slope value for more than the threshold amount of time; or determine not to instruct the patient to alter the medication regimen or cease the medication regimen based on the slope of the level of the substance over the period of time between the first time and the second time not being below the threshold slope value for more than the threshold amount of time.

8. The system of claim 1, wherein the medical device is further configured to collect a cardiac signal over the extended period of time greater than seven days, wherein the processing circuitry is further configured to:

receive, from the medical device, the cardiac signal;

identify, based on the cardiac signal, a heart failure event; and instruct the patient to begin the medication regimen based on identifying the heart failure event based on the cardiac signal.

9. The system of claim 1, wherein the processing circuitry is further configured to output, to a user interface of a clinician device, information indicative of a patient condition based on the trend.

10. The system of claim 1, wherein the medical device comprises:

one or more light emitters configured to output one or more emitted optical signals;

one or more light detectors configured to receive one or more reflected optical signals corresponding to the one or more emitted optical signals, and wherein the processing circuitry is configured to control the medical device to collect the optical biometric signal based on the one or more emitted optical signals and the one or more reflected optical signals.

11. A method of controlling operation of a system including a medical device configured to be implanted within a patient, the method comprising:

collecting, by the medical device, an optical biometric signal over an extended period of time greater than seven days, wherein the optical biometric signal indicates a level of a substance associated with a medication within the patient;

receiving, by processing circuitry of the system from the medical device, the optical biometric signal, wherein the processing circuitry is in communication with a memory;

identifying, by the processing circuitry based on the optical biometric signal, a first level of the substance;

determining, by the processing circuitry, a trend of the level of the substance between a first time corresponding to the first level of the substance and a second time following the first time; and determining, by the processing circuitry based on the trend, whether to instruct the patient to alter the medication regimen or cease the medication regimen.

12. The method of claim 11, wherein instructing the patient to begin the medication regimen comprises instructing, by the processing circuitry, the patient to take a medication including the substance.

13. The method of claim 11, wherein instructing the patient to begin the medication regimen comprises outputting, by the processing circuitry to a user interface of a user device, an instruction for the patient to take a medication for regulating a kidney function of the patient.

14. The method of claim 11, further comprising one of:

instructing, by the processing circuitry in response to determining to instruct the patient to alter the medication regimen or cease the medication regimen based on the trend, the patient to alter the medication regimen or cease the medication regimen; or instructing, by the processing circuitry in response to determining not to instruct the patient to alter the medication regimen or cease the medication regimen based on the trend, the patient not to alter the medication regimen or cease the medication regimen.

15. The method of claim 11, wherein the optical biometric signal comprises a fluoresced signal, wherein instructing the patient to begin a medication regimen comprises outputting, by the processing circuitry to a user interface of a user device, an instruction for the patient to take a medication comprising a fluorescent marker, wherein identifying the first level of the substance comprises determining, by the processing circuitry, a peak level of the fluorescent marker based on the fluoresced signal, and wherein determining the trend of the level of the substance comprises determining, by the processing circuitry, a trend of the level of the fluorescent marker between the first time and the second time.

16. The method of claim 11, wherein determining the trend of the level of the substance comprises, by the processing circuitry:

determining the level of the substance over a period of time between the first time and the second time; and determining a slope of the level of the substance over the period of time between the first time and the second time, wherein determining whether to instruct the patient to alter the medication regimen or cease the medication regimen based on the trend comprises determining, by the processing circuitry, whether the slope of the level of the substance over the period of time between the first time and the second time is below a threshold slope value for more than a threshold amount of time.

17. The method of claim 16, further comprising:

determining, by the processing circuitry, to instruct the patient to alter the medication regimen or cease the medication regimen based on the slope of the level of the substance over the period of time between the first time and the second time being below the threshold slope value for more than the threshold amount of time; or determining, by the processing circuitry, not to instruct the patient to alter the medication regimen or cease the medication regimen based on the slope of the level of the substance over the period of time between the first time and the second time not being below the threshold slope value for more than the threshold amount of time.

18. The method of claim 11, further comprising:

collecting, by the medical device, a cardiac signal over the extended period of time greater than seven days;

receiving, by the processing circuitry from the medical device, the cardiac signal;

identifying, by the processing circuitry based on the cardiac signal, a heart failure event; and instructing, by the processing circuitry, the patient to begin the medication regimen based on identifying the heart failure event based on the cardiac signal.

19. The method of claim 11, further comprising outputting, by the processing circuitry to a user interface of a clinician device, information indicative of a patient condition based on the trend.

20. A non-transitory computer-readable medium comprising instructions for causing one or more processors to:

control an implanted medical device to collect an optical biometric signal over an extended period of time greater than seven days, wherein the optical biometric signal indicates a level of a substance associated with a medication within a patient;

receive, from the medical device, the optical biometric signal;

identify, based on the optical biometric signal, a first level of the substance;

determine a trend of the level of the substance between a first time corresponding to the first level of the substance and a second time following the first time; and determine, based on the trend, whether to instruct the patient to alter the medication regimen or cease the medication regimen.

* * * * *